US009694177B2

(12) United States Patent
Berggren et al.

(10) Patent No.: US 9,694,177 B2
(45) Date of Patent: Jul. 4, 2017

(54) ELECTRICALLY CONTROLLED ION TRANSPORT DEVICE

(75) Inventors: Magnus Berggren, Vreta Kloster (SE); Joakim Isaksson, Waalre (NL); Edwin Jager, Linköping (SE); Peter Kjall, Lidingö (SE); David Nilsson, Vikingstad (SE); Agneta Richter-Dahlfors, Saltsjo-Boo (SE); Daniel T. Simon, Linköping (SE); Klas Tybrandt, Linköping (SE); Barbara Canlon, Saltsjo-Duvnas (SE)

(73) Assignee: OBOE IPR AB, Norrkoping (SE)

( * ) Notice: Subject to any disclaimer, the term of this patent is extended or adjusted under 35 U.S.C. 154(b) by 437 days.

(21) Appl. No.: 12/933,657

(22) PCT Filed: Mar. 20, 2008

(86) PCT No.: PCT/EP2008/002288

§ 371 (c)(1),
(2), (4) Date: Dec. 20, 2010

(87) PCT Pub. No.: WO2009/115103

PCT Pub. Date: Sep. 24, 2009

(65) Prior Publication Data

US 2011/0105997 A1 May 5, 2011

(51) Int. Cl.
*A61N 1/30* (2006.01)

(52) U.S. Cl.
CPC .................................... *A61N 1/306* (2013.01)

(58) Field of Classification Search
CPC .. A61B 5/14546; A61N 1/325; A61N 1/0428; A61N 1/306
USPC ........................................................... 604/20
See application file for complete search history.

(56) References Cited

U.S. PATENT DOCUMENTS

| | | | | |
|---|---|---|---|---|
| 6,875,613 | B2 * | 4/2005 | Shartle et al. | 436/63 |
| 8,805,522 | B2 * | 8/2014 | Chapman-Jones | A61N 1/326 607/2 |
| 2004/0267189 | A1 * | 12/2004 | Mavor | A61N 1/044 604/20 |
| 2007/0031341 | A1 * | 2/2007 | DiMauro | A61K 31/355 424/45 |

(Continued)

FOREIGN PATENT DOCUMENTS

| | | | |
|---|---|---|---|
| EP | 1862799 | A1 | 5/2007 |
| WO | 2006085908 | A | 8/2006 |
| WO | 2007119593 | A | 10/2007 |

OTHER PUBLICATIONS

International Search Report dated Jun. 9, 2009 in corresponding International Patent Application No. PCT/EP2008/002288, 4 pages.

(Continued)

*Primary Examiner* — Emily Schmidt
*Assistant Examiner* — Lauren M Peng
(74) *Attorney, Agent, or Firm* — Hultquist, PLLC; Steven J. Hultquist

(57) ABSTRACT

A device for electrically controlled of ions, comprises a first electrolyte; a first electrode, which is arranged in direct or indirect contact with the first electrolyte, an encapsulation; and an ion conductor, which is arranged to receive and/or deliver ions from/to the first electrolyte. The encapsulation is arranged to effectively enclose the first electrolyte, and the ion conductor is arranged to transport ions from/to an outside of the encapsulation.

8 Claims, 14 Drawing Sheets

(56) References Cited

U.S. PATENT DOCUMENTS

| | | | | |
|---|---|---|---|---|
| 2007/0313341 | | 2/2007 | Dimauro | |
| 2007/0135754 | A1* | 6/2007 | Akiyama | A61N 1/0444 604/20 |
| 2008/0161665 | A1* | 7/2008 | Ye | A61B 5/14542 600/348 |
| 2008/0161746 | A1* | 7/2008 | Visco | A61K 33/00 604/20 |

OTHER PUBLICATIONS

Philippe Schottland et al., "Poly(3,4-alkylenedioxypyrrole)s: Highly Stable Electronically Conducting and Electrochromic Polymers", Macromolecules 2000, 33, 7051-7061, 11 pages.

Mitsuyoshi Onoda and Hiroshi Nakayama, "Properties of Electrochemically Cation-Doped Poly(isothianaphthene)", J. Electrochem. Soc., vol. 141, No. 2, Feb. 1994, 4 pages.

J.C. Gustafsson, et al., "In situ spectroscopic investigations of electrochromism and ion transport in a poly (3,4-ethylenedioxythiophene) electrode in a solid state electrochemical cell", Solid State Ionics 69 (1994) 145-152, 8 pages.

J.M.J. Fre'chet, "Functional polymers: from plastic electronics to polymer-assisted therapeutics", Prog. Polym. Sci. 30 (2005) 844-857, 14 pages.

Arthur J. Epstein, Novel concepts in electronic polymers: polyaniline and its derivaties, Makromol. Chem., Macromol, Symp. 51, 217-234 (1991), 18 pages.

Prasanna Chandrasekhar, Conducting Polymers, Fundamentals and Applications—A Practical Approach, Kluwer Academic Publishers, 1999, 22 pages.

Gerhard Kossmehl and Gunnar Englemann, Application of Electrically Conductive Polythiophenes, Handbook of Oligo-and Polythiophenes, Wiley-VCH, Veriag GmH, 1999, 36 pages.

Response filed on Dec. 3, 2010 to the European Patent Office in corresponding European Patent Application No. 08734716.7, 3 pages.

* cited by examiner

ELECTRICALLY CONTROLLED ION TRANSPORT DEVICE

RELATED APPLICATIONS

This application claims benefit, under 35 U.S.C. §119, to International Patent Application No.: PCT/EP2008/002288, filed on Mar. 20, 2008, the disclosure of which is incorporated by reference herein in its entirety.

TECHNICAL FIELD

The present disclosure relates to an ion delivery and/or extraction device, to a system comprising such an ion delivery device and to its use.

BACKGROUND

Drug, or other chemical, delivery with both spatial and temporal control is often difficult with existing technologies. Delivery mechanisms are often either not bio-compatible for long periods of time (such as needles or metal-based implants), not temporally controllable (for proper dosing/delivery, such as pills, patches, etc.), or not targeted spatially (pills, patches, etc.). Providing control over drug delivery can be the most important factor at times when traditional oral or injectable drug formulations cannot be used. This can be due to low therapeutic effect of the drug when administered to the whole patient or that a drug is toxic except at the site where it exerts its action (e.g chemotherapeutic drugs in cancer treatment). Local delivery of drugs is also often needed due to the anatomical and cellular composition of the tissue or organ where adjoining cells should not be subjected to the drug. To achieve maximum control, the drug may need to be administered directly to its site of action, thus there is a need to develop drug delivery systems with spatial and temporal control.

The ideal in vivo drug delivery system should be inert, biocompatible, mechanically strong, comfortable for the patient, capable of achieving high drug loading, safe from accidental release, simple to administer and remove, and easy to fabricate and sterilize. Most contemporary systems meet some of these criteria but not all. Present systems use different methods of achieving in vivo release. Some are based on materials that allow constant passive diffusion of the drug to the tissue. In other systems, where a higher level of control is needed, release can be controlled by a system of micro-valves and pumps. These means of delivery have their disadvantages. Passive release systems lack control and can only allow a constant delivery of the drug. Systems based on micro-valves and pumps usually have the disadvantage that the mechanical parts are sensitive or prone to malfunction. Mechanical release devices are also very expensive due to their delicate components.

There is a need for a system that can be implanted, have strict electronic control over delivery providing high on/off ratios and at the same time allow for local delivery to small specific compartments in the body or even to single cells. The electronic control is crucial as it allows for customized release schedules and most importantly can eventually be coupled to sensors that can activate release upon a certain stimuli or need.

EP 1 862 799 A1, the entire contents of which, is incorporated herein by reference, discloses the general principles of an ion transport device, which is capable of electrically controlled transport of ions from a source electrolyte to a target electrolyte.

Such an ion transport has the spatial and temporal control desired for such a delivery device. However, in its described form, it is not feasible as an implant or as a self-contained device (for example, for use as a "smart-pipette").

Hence, there is a need for a device for a device and a system that enables delivery of ions in a spatially and temporally controlled manner.

SUMMARY

A general objective is to provide devices and systems, which eliminate or alleviate the problems of the prior art, or at least to provide a viable alternative to the prior art.

A specific objective is to provide devices and systems, which enable spatially and temporally controlled delivery of ions.

Yet another specific objective is to provide devices and systems, which enable spatially and temporally controlled delivery of ions in vitro and/or in vivo.

The invention is defined by the appended independent claims, with embodiments being set forth in the appended dependent claims, in the following description and in the drawings.

Under definitions herein below, the terms and expressions used in connection with this application are explained.

According to a first aspect there is provided a device for electrically controlled transport of ions, comprising, a first electrolyte; a first electrode, which is arranged in direct or indirect contact with the first electrolyte, an encapsulation; and an ion conductor, which is arranged to receive and/or deliver ions from/to the first electrolyte; wherein the encapsulation is arranged to effectively enclose the first electrolyte, and wherein the ion conductor is arranged to transport ions from/to an outside of the encapsulation.

By "outside of encapsulation" is meant a target region for the ions transported by the ion conductor. The target region may be any fluid, gel, hydrogel, semi-solid or solid material capable of receiving ions or other electrically charged molecules from an ion conductor. The outside may comprise, but is not limited thereto, liquids or cells e.g. in a laboratory experiment, bodily fluids, such as blood, urine, saliva, mucosal secretions, a cell surface, a tissue or an organ, in vivo or in vitro. The outside of encapsulation may also be a hydrogel arranged on the surface of the ion conductor.

The spatial limitation of the area defining the outside of encapsulation will be dependant on the configuration of the ion conductor and the capacity of the device for delivering/extracting ions.

By this device there may be provided a way of temporally and spatially controlling the delivery of ions to a specific region or target region, e.g. the delivery of a drug or substance to a specific area in the body such as a single nerve cell, or an entire organ. The electrical control may provide an on/off function of the delivery or extraction, which may contribute to a more even delivery of a drug. The electrical control may also provide a continuous or stepwise rate control.

According to the first aspect the ion conductor may present a pre-load region holding a first ion set, and wherein the ion conductor may be arranged to transport a second ion set from the first electrolyte and towards the pre-load region, so as to push the first ion set out of the ion conductor.

By this device there may be provided a way of more specifically controlling not only the temporal and/or spatial delivery of ions, but also the quantity of ions to be delivered, since the pre-loading region may be arranged to hold a predetermined amount of ions. The flow of the second ion set from the electrolyte to the electrode and/or ion conductor hence drives or "pushes" the first ion set from the ion conductor to the outside.

The second ion set may be such that it has no essential effect on the target region, or does not influence the action of the first ion set. The first and second sets of ions may be the same or different types of ions.

The pre-loading region may be realized by a portion of the ion conductor having an increased cross-section.

The ion conductor may be arranged to transport ions from/to the first electrolyte to/from the outside of the encapsulation.

The first electrode may be redox-active.

By utilising a redox-active material there may be provided a way of better controlling the transport of electrons and hence the transport of ions.

The first electrode may be formed of a solid or semi-solid material.

The first electrode and the ion conductor may be arranged as a unitary element, and may preferably be made from the same material.

By forming the electrode and ion conductor of the same material there may be provided an easy and simple way of manufacturing the device, and also a way of ensuring the proper transduction of ions.

According to the first aspect the device may further comprise means for applying a control signal to the first electrode.

By the provision of the control signal there may be provided a way of better controlling the transport of ions in a spatial and temporal manner.

The first electrode may be directly or indirectly attached to a support.

By attaching the electrode to a support there may be provided a way of increasing the durability and strength of the electrode, but it may also provide a possibility for controlling the area on which ions are able to enter the electrode from the electrolyte, by e.g. coating the electrode with an electrically insulating material over a portion(s) of the surface.

The encapsulation may also effectively enclose at least part of the first electrode.

By incorporating the first electrode into the encapsulation there may be provided a way of ensuring proper contact between the electrolyte and the electrode. The encapsulation may enclose the entire electrode, such that only the ion conductor protrudes from the encapsulation.

The encapsulation may, according to one alternative, be arranged such that a portion of the electrode also protrudes on the outside of the encapsulation.

The first electrode may be arranged as a coating on at least part of the encapsulation.

By arranging the electrode as a coating there may be provided a feasible way of manufacturing the device. The electrode may also be more durable by the support the encapsulation may provide.

The encapsulation may, according to one embodiment of the first aspect, be electrically and/or ionically insulating.

By insulation of the encapsulation there may be provided a way of ensuring that no undesired delivery and/or extraction of ions occurs outside the designated areas for this transport, i.e. through the ion conductor.

The ion conductor may comprise a first portion, which is arranged inside the encapsulation and in contact with the first electrolyte and/or the first electrode.

By arranging a first portion of the ion conductor within the encapsulation, there may be provided a way of transporting ions directly from the electrolyte to the ion conductor. A metal electrode may hence be used, since the ions from the electrolyte may move directly to the ion conductor.

The ion conductor may comprise a second portion, which is arranged outside the encapsulation for interaction with a surrounding environment.

The second portion of the ion conductor, arranged outside the encapsulation provides a way of delivering and/or extracting ions from the surrounding environment. This allows for a site directed delivery and/or extraction of ions from/to the electrolyte to/from the outside of the encapsulation.

The second portion may, according to one embodiment, connect to the encapsulation in a substantially continuous manner. Hence, the device may be formed with a minimum of protruding parts which may be damaged by, or damage, e.g. tissue which surrounds the device.

The second portion may be formed as a protrusion from a face of the encapsulation.

By "face" is meant essentially any side of a body of the encapsulation. By the second portion of the ion conductor being a protrusion there is provided a way of bringing the ion conductor in contact with the outside of the encapsulation, or a target region, such that ions may be transported to/from a specifically selected and well defined region in a satisfactory manner.

The second portion may, according to yet another alternative embodiment, present a tapering cross section.

By providing a tapering cross section it may be possible to decrease the area of contact between the ion conductor and the outside such that a very specific delivery or extraction of ions may be performed, i.e. a more well-defined spatial release. The second portion may hence be formed such that it may deliver/extract ions to/from a single cell or be inserted into a cluster of cells or tissue, e.g. a tumour.

The protrusion may present at least two ion conducting channels, the channels may be connected to separate source electrolytes or target electrolytes.

This embodiment may allow for multiple sources to be combined to the same release point, hence allowing for different types of ions to be delivered at the same time or sequentially. The provision of two or more ion conductive channels may also provide very well defined release areas.

The channels may, according to one embodiment, merge to form a single release portion, one of the channels may be connected to a source electrolyte and the other channel may be connected to a waste electrolyte, and the flow of ions through the channels may be individually controllable.

The second electrolyte may be a waste electrolyte, which may allow for an improved temporal control of ion delivery, since the ion conductive channel may be partially or fully filled with the ion to be transported by transporting the ion to the waste electrolyte, filling thereby filling the channel with ions, up to a point close to the release area, before the actual ion transport to the outside is initiated. The individual controllability may allow for the circuit to be changed to deliver ions from the source electrolyte to the outside of the encapsulation.

An insulation may, according to one embodiment, be provided on at least part of the protrusion.

By providing insulation, undesirable release of ions may be prevented until e.g. the end of the ion conductor or at any point along the ion conductor where the release is wanted. Hence a very defined release point or region may be achieved, e.g. even a specific face of a cell or an organ.

The protrusion may be substantially planar, or substantially tubular.

The shape of the protrusion will depend on the specific requirements of the application. The protrusion is not restricted to having the same geometry as the electrode. Hence the ion conductor may be substantially tubular and the electrode substantially planar or vice versa.

A protrusion is not necessary. The ion conductor may open directly at a face of the enclosure.

The first electrolyte may, according to one embodiment of the first aspect, be a source electrolyte, and the first electrode may be a source electrode, and the ion conductor may be arranged to transport ions from the first electrolyte to the outside of the encapsulation.

This device may allow for the transport of ions, from the source electrolyte to the outside of the encapsulation. The source electrolyte may comprise ions for, including but not limited to, altering a cellular response, or for turning on/off a cellular activity or for temporal/spatial control of a reaction in e.g. a test tube.

The first electrolyte may be a target electrolyte, and the first electrode may be a target electrode, and the ion conductor may be arranged to transport ions from the outside of the encapsulation to the first electrolyte.

This device may allow for the extraction of ions from a specific site, including, but not limited to, an organ or a cell; or for instance from a reaction mixture in a test tube, to the target electrolyte. The target electrolyte may then, subsequently to the extraction be analysed further, by methods well-know by a person skilled in the art. The device may also allow for the extraction of harmful substances from e.g. a cluster of cells or an organ.

The encapsulation may be formed as a substantially elongate body, having a length of about 1-100 mm, about 1-50 mm, or about 10-20 mm.

The ion conductor may be formed as a protrusion from the encapsulation, the protrusion extending about 0.001-20 mm, about 0.001-10 mm, or about 0.001-15 mm from the encapsulation.

The width of the ion conductor protrusion may be about 0.001-20 mm, about 0.001-10 mm, or about 0.001-15 mm. The protrusion may further be tapered, such that one end has a larger width than the opposite end.

According to the first aspect, the encapsulation may present an ion conducting portion, which may be arranged to form the first ion conductor. The device may further comprise a reinforcing support layer, which may be electrically insulating and ion conducting.

By this configuration there may be provided a way of constructing a multi-walled device, e.g. a multi-walled tube or box.

The device may further comprise an electrically and ionically insulating inner wall.

The first electrolyte may be arranged between the first electrode and the inner wall.

The electrolyte may be semi-solid, e.g. a gel and may hence substantially be an electrolyte wall.

The device may have an elongate, hollow structure and the first electrolyte may be arranged at or near a central portion of the structure. A central portion of the structure may provide a through channel.

By this configuration there may be provided a device where a liquid flow around the device is required, for example, but not limited to, in a catheter device where blood is required to maintain its flow.

The entire encapsulation, may according to one alternative, be ion conducting.

By the entire encapsulation being ion conducting there may be provided a device which is useful in applications where ions need to be delivered over an elongate area or surface or in the case of a tubular device a corresponding tubular area or surface, such as a blood vessel.

The encapsulation may present at least one portion which is ion conducting and at least one portion which is electrically and ionically insulating.

This device may provide a way of delivery of ions at specified locations along the length of the encapsulation.

The device may further comprise at least one region adapted for inserting or extracting the first electrolyte.

The region adapted for inserting or extracting the first electrolyte may be a port, a connector, a valve, a self-healing membrane, etc. This device may allow for a refill and/or exchange of electrolyte and/or of ions into the electrolyte, without the necessity for exchanging the entire device or encapsulated electrolyte. It may accordingly also allow for the extraction of electrolyte, e.g. for sampling of the electrolyte.

According to one alternative the device may comprise at least two such regions, where one may be used for refill of electrolyte/electrolyte liquid and the other for ventilation of any air/gas trapped inside the encapsulation. According to this alternative embodiment may the regions be placed at opposite ends of the device, which may be advantageous for venting trapped gas.

According to a second aspect there is provided a system comprising a device according to the first aspect, at least one second device for electrically controlled transport of ions, which comprises a second electrolyte; a second electrode, which is arranged in direct or indirect contact with the second electrolyte; and a second ion conductor, which is arranged to receive and/or deliver ions from/to the second electrolyte. The second ion conductor may be arranged to transport ions to/from the outside of the encapsulation.

Comparing to the device disclosed in EP 1 862 799 A1, the system does however not provide any direct ionic contact between the first and second electrode/electrolyte. By direct ionic contact is meant a substantial amount of ions comprised in the first material can move from the first material to the second material, via a third material (such as the ion conduction channel).

However the system may provide a way of delivering ions to the outside of the encapsulation, simultaneously or separately.

The devices may be attached to or separated from each other.

The encapsulated electrolytes of the different devices may comprise the same or different ionic species, thereby it may be possible to deliver e.g. two different types of drugs or substances to a specific region.

The devices may be identical in configuration or have different configurations, i.e. one device may be a tube with a strip as ion conductor, the other may be rectangular with a plug-shaped ion conductor.

The devices may be formed from the same or different materials.

The devices may be controlled individually, i.e. the ion transport of the different devices may be controlled for each device separately.

The second ion conductor may present a pre-load region holding a third ion set, and wherein the second ion conductor may be arranged to transport a fourth ion set from the second electrolyte and towards the pre-load region, so as to push the third ion set out of the second ion conductor.

By this device there may be provided a way of more specifically controlling not only the temporal and/or spatial delivery of ions, but also the quantity of ions to be delivered, since the pre-loading region may be arranged to hold a predetermined amount of ions. The flow of the fourth ion set from the electrolyte to the electrode and/or ion conductor hence drives or “pushes” the third ion set from the ion conductor to the outside.

The fourth ion set may be such that it has no essential effect on the target region, or does not influence the action of the third ion set.

The pre-loading region may be realized by a portion of the ion conductor having an increased cross-section.

The device, according to the first embodiment of the present solution, may also present a pre-loading region, wherein a second set of ions may be withheld.

The first and third ion sets may be the same or different types of ions.

The second and fourth ion sets may be the same or different types of ions.

The first and fourth ion sets may be the same or different types of ions.

The second and third ion sets may be the same or different types of ions.

The second ion conductor may be arranged to transport ions from/to the second electrolyte to/from the outside of the encapsulation.

The second electrode may be redox-active.

By utilising a redox-active material there may be provided a way of better controlling the transport of electrons and hence the transport of ions.

The system may further comprise a second encapsulation, and the second encapsulation may be arranged to effectively enclose the second electrolyte, and the second ion conductor may be arranged to transport ions between the second electrolyte, and an outside of the second encapsulation.

By this there may be provided a system with separate devices, i.e. the devices may be spaced apart from each other.

The first encapsulation may present at least two separate chambers, the first electrolyte may be arranged in a first chamber and the second electrolyte may be arranged in a second chamber. The chambers may be formed as separate lumens.

By this system the electrolyte/electrode systems may be provided as a compact device. The number of chambers is limited/determined by the application/need.

The chambers may, according to one embodiment, be formed as longitudinally juxtaposed chambers.

The first and second ion conductors may form channels which open towards the outside at the same face of the encapsulation.

At least one of the first and second electrodes of the system may extend through the second or first electrolyte, respectively, and is electronically and ionically insulated from said second or first electrolyte.

The insulation may prevent undesired leakage of ions from the first or second electrode to the second or first electrolyte, respectively.

The first and second ion conductors may form channels which open at different faces of the encapsulation.

Hence, delivery may be provided to different target regions, or to different parts of the same target region.

The system may further comprise means for limiting an electronic current between the first electrode and the second electrode, such that at least after a voltage is applied across the ion conductor, a potential difference between the first electrode and the second electrode is maintained, which effects ion transport between the first electrode and the second electrode.

The second electrolyte may be a source electrolyte, and the second electrode may be a source electrode, and the ion conductor may be arranged to transport ions from the second electrolyte to the outside of the encapsulation.

This device may allow for the transport of ions, from the source electrolyte to the outside of the encapsulation. The source electrolyte may comprise ions for altering a cellular response, or for turning on/off a cellular activity or for temporal/spatial control of a chemical reaction in e.g. a test tube. By chemical reaction is meant e.g. polymerisation reactions; isomerisation; biochemical reactions, e.g. enzymatic reactions; substantially inorganic reactions, such as chemical decomposition, substitutions reactions, combination reactions, metathesis reactions, acid-base reactions, red-ox reactions, precipitation reactions; substantially organic reactions, such as addition, elimination, substitution, pericyclic, rearrangement and red-ox reactions. The second electrolyte may be a target electrolyte, and the second electrode may be a target electrode, and the ion conductor may be arranged to transport ions from the outside of the encapsulation to the second electrolyte.

This device may allow for the extraction of ions from a specific site, including, but not limited to, an organ or a cell; or for instance from a chemical reaction mixture in a test tube, to the target electrolyte. The target electrolyte may then, subsequently to the extraction be analysed further, by methods well-know by a person skilled in the art. The device may also allow for the extraction of harmful substances from e.g. a cluster of cells or an organ.

According to a third aspect there is provided a system comprising a device according to the first aspect or a system according to the second aspect; and a counter electrode.

By the provision of a counter electrode there is provided means for closing the electrochemical circuit, which is the driving force of the ion transport.

The counter electrode may be arranged such that it in some way contacts the outside of the encapsulation, i.e. the target region for the delivery/extraction of ions from/to the ion conductor of the encapsulated electrolyte device.

The system according to the third aspect may further comprise means for limiting an electronic current between the first electrode and the counter electrode, such that at least after a voltage is applied across the ion conductor, a potential difference between the first electrode and the counter electrode is maintained, which effects ion transport between the first electrode and the counter electrode.

By the ability of limiting or controlling the electronic current between electrodes and hence influence the ion transport there may be provided a way of temporally and spatially controlling the delivery of ions to/from the outside of the encapsulation.

The counter electrode may be separate from the encapsulation.

This configuration provides a system where the counter electrode may be placed arbitrarily in relation to the encapsulation. The counter electrode may also easily be replaced, e.g. if it has been worn out.

The counter electrode may, according to one embodiment, be attached to the encapsulation.

This configuration may provide a compact system and means for controlling the position of the counter electrode in relation to the encapsulation.

According to a fourth aspect there is provided a structure adapted for insertion into an animal body, comprising a device according to the first aspect or a system according to the second and third aspects.

By a "medical device" is meant, but not limited thereto, a surgical tool; a catheter or catheter system (balloon catheter, guide catheter, etc.) as well as devices positioned by means of catheters, like clamps, forceps, expandable tubes, constricting tubes, etc.; grafts, orthopaedic implants, dental implants, fixation screws, ocular implants, pharmacotherapeutic implants, blood-contacting components of extracorporeal devices, staples, filters, needles, tubes, coils, wires, clips, screws, sensors, plates, conduits portions thereof or combinations thereof.

The device may, for instance, be integrated into or onto the medical device.

By this arrangement the encapsulated electrolyte device may influence, i.e. improve/increase or alter, the functionality of the medical device.

The encapsulated electrolyte device may e.g. be pre-assembled with the medical device during manufacture thereof, or it may be attached to the device as a cartridge or patch before surgical procedure by the medical professional.

According to the fourth aspect, a part of the ion conductor may be exposed at an externally facing portion of the medical device.

By this arrangement the device may be introduced into the body at the same time as the medical device and may be used to deliver e.g. a drug to the same area as the medical device is meant to operate in/on. The ion delivery and/or extraction device may further be arranged to influence the functionality of the medical device or alter the environment surrounding the medical device in order to increase/improve its functionality.

The medical device may comprise a radially expandable portion, and wherein the exposed part of the ion conductor is positioned at least partially on the expandable portion.

According to a fifth aspect there is provided an ion delivery and/or extraction device comprising a device according to the first aspect, a system according to the second and third aspects or a medical device according to the fourth aspect, and a control unit, arranged to control the transport of ions to/from the first electrolyte.

By "control unit" is meant an electronic system for applying a voltage to the device.

The control unit which controls the transport of ions to/from the first electrolyte may provides a way of controlling the transport of ions temporally, i.e. provide an on/off function. Thus, the present disclosure may involve limiting an electronic current, i.e. a current or flow of electrons, in a material, while maintaining the ion conductivity of the material. A limitation of the electronic current in the material can e.g. be achieved by limiting the electron conductivity. This limitation makes it possible to maintain a potential difference over the material when a voltage is applied across it. The potential difference can then be used as a driving force for ion transport from one portion of the material to another.

The control unit may be integrated with the ion delivery and/or extraction device.

The control unit may be incorporated into the device, either immediately adjacent to the encapsulated electrolyte or at some distance away.

By integrating the electronic control with the ion delivery and/or extraction device is provided a device which may be inserted into the body, without the necessity for physical contact with the outside of the body, i.e. without the need for e.g. wires leading from the device to the outside. This may contribute to reducing the risk of infections and discomfort of the patient into whom the device has been inserted.

The control unit may, according to one embodiment, be connectable to the device.

By a connectable control unit is meant e.g. a laboratory power supply controlled by a personal computer.

A connectable control unit may allow for the unit to easily be replaced or exchanged.

The first control unit portion may be integrated with the device, and the second control unit portion may be separable from the first control unit portion.

The connection between the first and second portion may be a cable, a wire or wireless, e.g. by IR, Bluetooth or radio or any other means for wireless communication, known by a person skilled in the art.

The ion delivery and/or extraction device, according to the fifth aspect may further comprise a sensor in communication with a control unit and arranged to provide feedback.

By this arrangement there may be provided a way of further controlling the delivery and/or extraction of ions from/to the first electrolyte. The sensor may be arranged to detect a specific ionic species on the outside of the encapsulation or within the encapsulation and/or both, and submit a control signal to the control unit, thereby influencing the voltage applied and hence the delivery/extraction of ions.

The sensor may be arranged to detect the ionic species which is delivered/extracted from/to the first (or source) electrolyte, but it may also be arranged to detect a different ionic species, or any other parameter suitable for the application. The sensor may for instance be arranged to detect a metabolite excreted from a cell as a biological response to an ion delivered to the cell by the device. The sensor may also be arranged to detect a change in pH, or temperature. The suitable detection parameters of the sensor are readily conceived by a person skilled in the art.

The ion delivery and/or extraction device may comprise a main body having a receptacle, and the encapsulation may be formed as a cartridge, which may be adapted to be received in the receptacle.

By this configuration there may be provided a device, which may be used as an electronically controlled pipette or "smart pipette" with an exchangeable cartridge. Since the cartridges may be pre-filled with electrolyte this device may be simple and fast to use. The smart pipette allows for a well defined delivery and/or extraction of ions both spatially and temporally, depending on the design of the device and the voltage applied to the device.

The cartridge may hence comprise the encapsulation containing the electrolyte, the electrode and the ion conductor. The cartridge may also be provided with regions for extracting and/or inserting electrolyte, such as a port, a connector, a self-healing membrane or a valve, and may hence provide a reusable cartridge system. This may also e.g. provide a possibility for extracting samples from the electrolyte, during or after an experiment.

The main body may comprise a control unit and a connector for interaction with a corresponding connector on the cartridge.

This configuration may provide a simple and fast way of attaching the cartridge to the device.

The device may comprise a user interface.

A user interface may comprise one or more input and/or output devices, which may be optical, mechanical, audible and/or tactile. The user interface may allow for the user to control the voltage applied to the device, and hence temporally and spatially control the delivery of ions. The main body may comprises a power source.

The main body may comprise a counter electrode.

The counter electrodes provides a way to close the electronic circuit needed for the transport of ions from/to the first (source) electrolyte.

According to a sixth aspect there is provided a method of operating a device, a system, a medical device, or an ion delivery and/or extraction device set forth above, wherein a control signal is provided to the first electrode such that ions are caused to be transported from/to the outside of the encapsulation.

The outside of the encapsulation may be an in vitro environment. The ions may be delivered to or extracted from a cell, a cluster of cells, or a cell culture.

By this method the delivery/extraction of ions from/to the first electrolyte may be temporally and spatially controlled for instance in laboratory trials and experiments. The device may be used as an electronically controlled pipette, or a "smart pipette" for delivery and/or extractions of ions at very well-defined sites, such as a cell or a cluster of cells on a Petri dish. This method may also allow for studies of excreted substances from cells, since these may be extracted and transported to the encapsulated electrolyte for further analysis.

In the alternative, the outside of the encapsulation may be an in vivo environment.

By this method the delivery/extraction of ions from/to the first electrolyte may be temporally and spatially controlled, which may be useful in administering, to a patient in need thereof, an electrically charged substance, such as an endogenous substance or a synthetic or natural drug, in order to remedy, cure or prevent a disease or disorder. By the spatial control provided by the method a very specific site in the body may be treated, such as a nerve cell or a specific portion of an organ. The temporal control may provide a safer and more controlled way of delivering a therapeutically active substance to a patient during a period of time, in which the device is in contact with the body.

According to the seventh aspect the ions may be delivered to or extracted from a cell, a cluster of cells, a tissue or an organ.

The term "cell" is meant to encompass all types of animal cells that may be of interest for treatment of certain diseases or disorders. Non limiting examples of types of cells that may be used with the present disclosure include eukaryotic cells which are cells with nucleus and prokaryotes which are cells without nucleus. Non limiting examples of eukaryotic cells include stem cells and other nerve cells, cells present in the immune system, epithelial cells, and endothelial cells. Non limiting examples of prokaryotic cells include different kinds of bacteria. A person skilled in the art of cellular research would readily be able to name any number of different cells that may be used with the present disclosure.

Cell sizes of cells useful with the present disclosure are typically in the range of 1 μm-1 mm and may for example be in the range of 10-500 μm in diameter or in the range of 10-100 μm or 10-50 μm. Also some types of cells that may be of interest will be straggling.

With a cluster of cells, as the term is used in the present disclosure, is meant a number of adjacent cells ranging from 2 cells to millions of cells. Typically a cluster of cells may comprise about 2-1 000 000 cells, for example about 100 000-1 000 000 cells. One specific cluster of cells could be a tumor. A person skilled in the art of cellular research would readily be able to name other types of cell clusters that may be of interest to study using a device according to the present disclosure.

By "tissue" is meant a group of cells united to perform a specific function, a tissue may also be a part of an organism consisting of an aggregate or cluster of cells having similar structure and function. The term tissue includes, but is not limited to, epithelium, connective tissue, muscle tissue and nerve tissue. A tissue may also be a benign or malignant tumor, i.e. an abnormal mass of tissue.

By "organ" is meant a natural part or structure in an animal, capable of performing some special action, including, but not limited thereto, the organs of the bowel system, skeletal system, muscle system, circulatory system, nervous system, respiratory system, digestive system, excretory system, endocrine system, reproductive system, lymphatic/immune system. Examples of organs thereof include, but is not limited to, bones, cartilage, tendons, ligaments; skeletal and smooth muscles; heart, blood vessels, blood; brain, spinal cord, peripheral nerves; nose, trachea, lungs; mouth, esophagus, stomach, small and large intestines; kidneys, ureter, bladder, urethra; glands such as hypothalamus, pituitary, thyroid, pancreas and adrenal; ovaries, oviducts, uterus, vagina, mammary glands, testes, seminal vesicles, penis; and lymph, lymph nodes and vessels, white blood cells, T- and B-cells.

The device or system may be implanted into a body.

By "implanted into a body" is meant that the device is put brought into the body or attached to it, as a prosthesis, or for treatment and/or diagnosis. By implanting the device there may be a way of more or less permanently delivering ions to or extracting ions from a cell, a cluster of cells, a tissue or an organ, such as described above. The implant may be put into place by surgical procedures to reinforce or replace a part of the body, to control the function of an organ or to keep an anatomical channel open.

By this device there may be provided a way of temporally and/or spatially controlling the delivery of, e.g. drugs or endogenous substances to a patient in need thereof.

By "adapted for insertion" is meant that the device is formed by biocompatible materials and is of a size suitable for the application, in which it is intended for. Alternatively only portions of the device, i.e. those which are intended for contact with the body are formed by biocompatible materials.

By "body" is meant the human body, or the body of any living organism such as a vertebrate or an invertebrate animal, comprising, but not limited thereto, a mammal, such as a human, a dog, a cat, a horse, a guinea pig, a pig, a sheep, a cow, a rabbit, a hamster, a monkey, a mouse, a rat etc.

The device may be temporarily inserted into the body/brought into contact with the body.

By "temporarily inserted" is meant that the device is introduced in the body for a relatively short period of time, e.g. during a surgical procedure, or during a period in which a patient is staying at a hospital.

According to an eighth aspect there is provided a method of treating and/or preventing a disease or disorder in an animal by controlling the release of an active agent. The method comprises providing a device, a system, a medical device, or an ion delivery and/or extraction device as set forth above, configured and dimensioned to be used within a body of an animal. The method further comprises bringing the device into contact with the body of the animal; and applying a control signal to the device, thereby causing the active agent to be released from said ion conductor to the outside of the encapsulation.

By "bringing into contact" is meant that the device may touch, be implanted in, or temporarily inserted into, the body of the animal.

The method may further comprise placing said device into or in contact with a body, a fluid, an organ, a tissue, a cell or a cluster of cells of an animal.

The method, according to the eighth aspect, may further comprise ionically conducting, from at least one ion conductor, a therapeutically effective amount of said active agent to treat and/or prevent a disease or disorder in which said active agent is effective as a therapy.

Furthermore, the method may include the use of a sensor to directly or indirectly detect a physiological parameter, the release of the active substance and/or detect a biological response, and to adjust the release of the active agent at least partially based on the signal from the sensor. The sensor may be arranged to detect the ionic species which is delivered/extracted from/to the first (or source) electrolyte, but it may also be arranged to detect a different ionic species, or any other parameter suitable for the application. The sensor may for instance be arranged to detect a metabolite excreted from a cell as a biological response to an ion delivered to the cell by the device. The sensor may also be arranged to detect a change in pH, or temperature. In another configuration, the sensor may be arranged to measure a physiological parameter that would necessitate the delivery of ions, i.e. the threshold level at which to administer the ions, the sensor may e.g. measure the glucose level in the blood in order to control the release of insulin from the device.

The suitable detection parameters of the sensor are readily conceived by a person skilled in the art. By this arrangement a more well designed dosage of an active substance, to a patient in need thereof, may be achieved. By measuring the amount of ions released by the device, or e.g. a biological response, and correlating this detection to the desired effect of the released substance or the biological response, an adjustment of the release of ions may be performed, i.e. by the control unit providing the device with a control signal.

The active agent may comprise at least one of said active agent comprises at least one of analgesics, antipyretics, antiasthamatics, antibiotics, antidepressants, antiepileptics, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, antipruritics, agents useful for calcium regulation, antibacterial agents, antiviral agents, antimicrobials, anti-infectives, broncho dilators, neurotransmittors, peptides, amino acids, DNA, DNA fragments, DNA sequences, plasmids, proteins, vitamins, steroidal compounds and hormones, or combinations thereof.

The active agent may, according to one embodiment comprise any one of acetylcholine, aspartate, dopamine, norepinephrine, serotonin, histamine, epinephrine, ATP, GTP, gamma-aminobuturic acid, glutamate, aspartate, glycine, tryptophan, adenine, guanine, cytosine, thymine, adenosine.

The active agent may be a charged species.

The term "charged species" as used herein encompasses not only positively or negatively charged monovalent or multivalent ionic species of atomic elements, but also other molecular species carrying a net positive or negative charge, the term "ions" as use herein is hence also meant to encompass all of these "charged species". The terms charged species and ions will be used interchangingly. Hence, in an embodiment of the present disclosure, it is intended to transport charged biologically active molecules or macromolecules such as charged amino acids, DNA, DNA sequences/fragments or plasmids, proteins, vitamins, peptides or hormones.

The "charged species" or "ions" as such may hence be endogenous or synthetic molecules. In one embodiment, the ions that may be transported are cations, for example metal ions, such as potassium or calcium ions. In another embodiment, the ions that may be transported are anions. The transported "ions" may act as stimuli for the cells. These stimuli may turn on a cellular process or turn off a cellular process, or act as an inhibitor. A non-limiting example is potassium which may act as stimuli for neuronal cells by opening the voltage-operated $Ca^{2+}$ channels in the cell membrane. A non-limiting example of an inhibitor may be cadmium which may block the voltage-operated $Ca^{2+}$ channels in the cell membrane. The term "charged species" also encompasses species that may be charged by setting a certain pH of the electrolyte solution or channel. The pH needed to charge these species may be calculated from the pKa of these molecules. The term ion also encompasses molecules which may be chemically modified to obtain a net charge, e.g. by attaching an ion to them.

The disease or disorder, according to the eighth aspect may be any one of a neurological, a CNS, a hearing, a muscle, a cardiac, an autoimmune, disease or disorder.

The disease or disorder may be epilepsy. The disease or disorder may be Parkinsons disease. The disease or disorder may be Alzheimers disease. The disease or disorder may be myasthenia gravis. The disease or disorder may be facial paresis. The disease or disorder may be stroke. The disease or disorder may be a disorder in the sphincter muscles, and may be achalasia.

Definitions

By the term "semi-solid material" is meant a material, which at the temperatures at which it is used has a rigidity and viscosity intermediate between a solid and a liquid. Thus, the material is sufficiently rigid such that it does not flow or leak. Further, particles/flakes in the bulk thereof are substantially immobilized by the high viscosity/rigidity of the material.

The semi-solid material may have the proper rheological properties to allow for the ready application of it on a support as an integral sheet or in a pattern, for example by conventional printing methods. After deposition, the formulation of the material should preferably solidify upon evaporation of solvent or because of a chemical cross-linking reaction, brought about by additional chemical reagents or by physical effect, such as irradiation by ultraviolet, infrared or microwave radiation, cooling etc.

The semi-solid or solidified material may comprise an aqueous or organic solvent-containing gel, such as gelatin or a polymeric gel.

With respect to the present disclosure, the term "electrochemically active material" refers to a material which may comprise a proportion of a component in an electrochemical reaction when it is in contact with an electrolyte and a voltage is maintained across it. Examples of such electrochemically active materials include electrically conductive polymers, as will be described below; and certain metal oxides, such as indium tin oxide (ITO), nickel oxide (NiO), manganese dioxide (MnO2) and tungsten oxide (WO3).

By "electrolyte" is meant a solvent which permits ionic conduction in the electrolyte, i.e. which allows for the dissociation of ionic substances such as salts, acids, bases etc. The solvent and/or the ionic substance may contribute nucleophiles. Possible electrolytes for use in combination with the device are solutions of salts, acids, bases, or other ion-releasing agents in solvents that support the dissociation of ionic species, thus allowing ionic conductivity. In applications where it is required, the electrolytes may comprise buffer solutions, such as buffer solutions suitable for use with living organisms or biomolecules, such as proteins. Examples of such buffers include $NaHPO_4$ and sodium acetate. As other non-limiting examples of possible electrolytes, mention can be made of: aqueous solutions of potassium acetate, calcium acetate, NaCl, $Na_2SO_4$, HCl, $H_3PO_4$, $H_2SO_4$, KCl, $RbNO_3$, $NH_4OH$, CsOH, NaOH, KOH, $H_2O_2$; Ringer's solution, organic solvents such as acetonitrile, pyridine, DMSO, DMF, dichloromethane, etc., in combination with suitable salts, such as lithiumperchlorate and tertiary ammonium salts, e.g. tetra-butyl ammonium chloride; inorganic solvents such as hypercritical $CO_2$, liquid $SO_2$, liquid $NH_3$, etc., in combination with salts that dissociate in these solvents; solvents displaying auto-dissociation, which results in the formation of ionic species, such as water, formic acid and acetic acid. The term electrolyte also encompasses solutions comprising charged biologically active molecules or macromolecules such as charged amino acids, DNA, DNA fragments and plasmids, proteins, vitamins, peptides or hormones. An electrolyte may also comprise cell culturing media or ingredients thereof, such as proteins, amino acids, vitamins, and growth factors.

The electrolyte may also be in a semi-solid or solidified form, preferably comprising an aqueous or organic solvent-containing gel as described hereinbelow. However, solid polymeric electrolytes are also contemplated and fall within the scope of the present disclosure. Furthermore, the term electrolytes also encompasses liquid electrolyte solutions soaked into, or in any other way hosted by, an appropriate matrix material, such as a paper, a fabric or a porous polymer.

The electrolyte also includes so called ionic liquids, which is liquids that contains essentially only ions. Examples of these are quarterial ammonium salts, phosphonium salts, mixtures of 1,3-dialkylimidazolium or 1-alkylpyridinium halides and trihalogenoaluminates, EMIM $EtOSO_3$ (1-Ethyl-3-methylimidazolium ethylsulfate), LiClO4 dissolved in 1-butyl-3-methylimidazolium tetrafluoroborate.

The electrode(s) of the device comprise an electrochemically active material. In a preferable configuration the electrodes comprise a material or a combination of materials which are capable of conducting both ions and electrons. In a more preferable configuration the molecular structure of the electrode allows for ions of at least a low molecular weight to enter the electrode via an electrolyte in ionic contact with the material, and for these ions to move within the material with some degree of freedom.

Ion conductivity and electron conductivity may be provided by the same material. Examples of materials which are able to conduct both ions and electrons are some electrically conductive polymers as will be described in greater detail below. An advantage of conducting polymers may be that no harmful reaction products are created in the redox reactions.

It is also possible to use a combination of two or more materials where at least one of the materials is electronically conductive and at least one of the materials is capable of conducting ions. Examples of such combinations, which may be used in a device according to the present disclosure, include an electronically conductive material, such as indium tin oxide, and an ion-conductive hydrogel.

The electrode(s) may also comprise further organic or inorganic materials, which are capable of conducting ions but not capable of conducting electrons, which materials are included in order to facilitate ion transport into and within the electrode(s). Non-limiting examples of such materials are polymer materials, such as hydrogels and polyelectrolytes. Such additional electrode materials may be either dispersed in, or be arranged as a separate layer in contact with, an electronically conductive electrode material.

The electrode(s) of the device may comprise an electrochemically active material. Preferably, said electrode material is an organic material. More preferably said organic material is a polymer, and may be an electrically conductive polymer. Electrically conductive polymers suitable for use in the device of the present disclosure, are preferably selected from the group consisting of polythiophenes, polypyrroles, polyanilines, polyiso-thianaphthalenes, polyphenylene vinylenes and copolymers thereof such as described by J C Gustafsson et al. in Solid State Ionics, 69, 145-152 (1994); Handbook of Oligo- and Polythiophenes, Ch 10.8, Ed D Fichou, Wiley-VCH, Weinhem (1999); by P Schottland et al. in Macromolecules, 33, 7051-7061 (2000); by M Onoda in Journal of the Electrochemical Society, 141, 338-341 (1994); by M Chandrasekar in Conducting Polymers, Fundamentals and Applications, a Practical Approach, Kluwer Academic Publishers, Boston (1999); and by A J Epstein et al. in Macromol Chem, Macromol Symp, 51, 217-234 (1991). In one especially preferred embodiment, the electrically conductive polymer is a polymer or copolymer of a 3,4-dialkoxythiophene, in which said two alkoxy groups may be the same or different or together represent an optionally substituted oxy-alkylene-oxy bridge. It is particularly preferred that the polymer is a polymer or copolymer of a 3,4-dialkoxythio-phene selected from the group consisting of poly(3,4-methyleneioxythio-phene), poly(3,4-methylenedioxythiophene) derivatives, poly(3,4-ethylenedioxythiophene), poly(3,4-ethylenedioxythiophene) derivatives, poly(3,4-propylenedioxythiophene), poly(3,4-propylenedioxythiophene) derivatives, poly(3,4-butylenedioxythiophene), poly(3,4-butylenedioxythiophene) derivatives, and copolymers therewith.

In one embodiment of the device, said electrically conductive polymer is poly(3,4-ethylenedioxythiophene) (PEDOT). Preferably the electrode(s) further comprises a polyelectrolyte compound, more preferably said poly-electrolyte compound is poly(styrene sulfonic acid) or a salt thereof. One especially preferred material for use in the electrode(s) of the device of the present disclosure is poly(3,4-ethylenedioxythiophene) with a poly(styrene sulfonate) polyanion (in the following referred to as PEDOT:PSS). In an embodiment the electrode(s) is present in the form of a thin layer of PEDOT:PSS deposited on a solid substrate.

The electrode(s) of the device may further comprise a hydrogel. The hydrogel is preferably based on polymers selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA), polysaccharides, such as agarose, chitosan and dextran, gelatin, polyvinyl alcohol, polyvinyl pyrrolidone, polyethylene oxide and polyethylene glycol.

In an embodiment the electrode(s) is present in the form of a thin layer of PEDOT:PSS deposited on a solid substrate and a thin layer of chitosan deposited on said PEDOT:PSS layer. Other combinations of materials can also be used.

The electrodes, in particular any counter electrode, may also be formed by carbon, or any suitable metal readily conceived be a person skilled in the art.

The electrode(s) may be arranged in a common plane on a solid substrate. Preferably the electrode(s) may be deposited onto said substrate by printing or lamination techniques. Use of printing methods in combination with conventional semiconductor processing methods, such as lithography and etching, allows for the electrodes to be patterned with a resolution of about 1 μm. This allows the device to be manufactured in miniature scale, which e.g. is useful in biochemical and cell applications where samples and preparations may be available only in very minute amounts. Preferably the thickness of the electrodes is less than 1 mm. The thickness is measured in a direction normal to the support on which the electrode is arranged.

An embodiment of the device is provided, in which at least one of the electrodes is biocompatible. The term biocompatible is used herein to characterize a material or a surface allowing cultivation of cells thereon or in close association therewith or to a material suitable for insertion into a living organism and/or for more or less permanent contact with tissues and fluids in the body without causing an inflammatory response.

The material should further be suitable for storage and transportation and be suitable for long-time insertion in a body, i.e. not be susceptible to degradation by the biochemical environment, such as body fluids and compounds and substances excreted by cells and/or organ systems. Cultivation of cells refers to attachment, maintenance, growth and/or proliferation of said cells. An example of an electrode material that provides a biocompatible surface is PEDOT:PSS. The biocompatibility of an electrode allow for studies of cellular activities in cells cultivated on or in close association with the electrode and in vivo use.

The ion conductor used may be made of a solid or semi-solid material which is able to conduct ions. According to one embodiment, the ion-conductive channel is essentially electronically non-conductive, i.e. the capability of conducting electrons is substantially limited. When reference is made to the ion-conductive channel being or being rendered “essentially non-conductive” or simply “non-conductive”, those terms are intended to encompass completely insulating materials as well as materials which have been rendered sufficiently deactivated and insulating to be useful e.g. as an electrically insulating barrier between areas of the polymer that have not been rendered essentially non-conductive. Such essentially non-conductive polymers have preferably had their conductivity reduced by a factor greater than $10^2$, and even more preferably greater than $10^5$. Thus, to render a polymer essentially non-conductive or to render a polymer non-conductive is, for the purpose of the present disclosure, to be interpreted as the action of substantially reducing the conductivity of the polymer.

When a voltage is applied across an ion conductor that has a limited electron conductivity, a potential difference between anode and cathode will be maintained. The potential difference generated will affect transport of ions present in the ion conductor or in the ion-conductive electrode connected to the ion conductor. The mechanism behind the ion transport has not been fully elucidated. It should be pointed out, however, that the present disclosure does not depend on any particular theoretical explanation. Neither does the skilled person need to rely on any particular theoretical foundation.

The capability of the ion conductor of being ion-conductive, whilst being essentially electronically non-conductive, may be inherent in the material used. Some materials that could be used as ion conductors in the ion conductors of the device include polyelectrolytes such as poly(styrene sulfonic acid) (PSS) and poly(acrylic acid) or hydrogels based on polyacrylates, such as poly(2-hydroxyethyl methacrylate) and poly(acrylamide), polyelectrolytes, such as poly(styrene sulfonic acid) (PSS) and poly(acrylic acid) (PAA) and derivatives thereof, polysaccharides and derivatives thereof, such as agarose and dextran, protein based gels such as gelatin and other water soluble polymers, such as polyvinyl alcohol, polyethylene oxide, polyvinyl pyrrolidone, polyethylene glycol and chitosan. Ionic liquids in a semi-solid state could also be used. Other examples of materials which are inherently ion-conductive and essentially electronically non-conductive include conductive polymers such as those mentioned above, which have been overoxidized and thereby rendered electronically non-conductive. In context of the present disclosure, an overoxidized state is a non-reversible electronically non-conducting state of the material.

In some embodiments, the material used in the ion conductor may be the same as a material used to facilitate ion transport in the electrode. For example, the ion conductor may comprise a hydrogel in order to facilitate ion transport.

Preferably the ion conductor comprises an organic material, more preferably said organic material comprises a polymer. The polymer may preferably be a hydrogel based on a polymer selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA) and derivatives thereof, polysaccharides and derivatives thereof, such as agarose and dextran, protein based gels such as gelatin and other water soluble polymers, such as polyvinyl alcohol, polyethylene oxide, polyvinyl pyrrolidone and polyethylene glycol. The ion conductor may also comprise a polyelectrolyte, such as for example poly(styrene sulfonic acid) (PSS) or poly(acrylic acid).

In an embodiment of the device, the ion conductor may comprise an over-oxidized electrically conductive polymer material, preferably over-oxidized poly(3,4-ethylenedioxythiophene):poly(styrene sulfonic acid) (PEDOT:PSS).

In a another embodiment, the ion conductor, which is used to ionically connect the first electrode and the outside, comprises the same conductive polymer as that present in said electrode, with the difference that the conductive polymer present in the ion conductor has been overoxidized, i.e. its electron conductivity has been permanently reduced by means of oxidation.

In a preferred embodiment, the device may be all-organic, i.e. all materials present in the device are organic. One advantage of all-organic devices is that they may be more readily recycled than devices comprising a combination of organic and inorganic materials that may require disassembly prior to recycling.

An inherent advantage of a device according to the present disclosure may be the low voltage required to effect ion transport from a source to a target electrolyte.

Magnitude and polarity of the voltages to be applied in the device and method will vary depending on a number of factors, such as choice of electrode material(s), the ion to be transported, the distance over which the ions are transported, etc. The polarity of the applied voltages will easily be selected by a person skilled in the art, taking into account the type of charge (positive or negative) of the ion to be transported. The magnitude of the voltage to be applied may, in the light of the present disclosure, easily be determined in order to transport a desired amount of ions.

The voltage applied across the ion conductive channel may for example be within the range of from about 0.01 V to about 100 V. The optimal voltage to apply between electrodes will depend on the characteristics of the polymer used, the electrolyte used, the ion to be transported and the manner in which the voltage is applied to the interface between polymer and electrolyte. However, the voltage is preferably in the range of from 0.001 V to 100 V, more preferably in the range of from 0.01 V to 20 V.

In the ion pump devices, reference is made to an insulation material. These materials may be either electrically insulating, ionically insulating or both electrically and ionically insulating at the same time. The insulation material may or may not be photopatternable. They encompass/comprise polymers such as photo resists including SU-8, polyimide, different kinds of lacquer such as acrylic resin, evaporation of oxides such as $SiO_2$, or nitrides such as $Si_3N_4$, spin on glass, ceramics, lamination foils.

In the present disclosure, reference is made to an encapsulation material. This material may be either electrically insulating, ionically insulating or both electrically and ionically insulating at the same time. The encapsulation material may or may not be photopatternable. They encompass/comprise polymers such as photo resists including SU-8, polyimide, different kinds of lacquer such as acrylic resin; evaporation of oxides such as $SiO_2$, or nitrides such as $Si_3N_4$, spin on glass; ceramics; lamination foils; silicone materials, e.g. tubing; plastic and polymer materials, etc.

The encapsulation material is preferably biocompatible and made from a material which is readily realized by a person skilled in the art, suitable for inserting into a living organism and/or for more or less permanent contact with tissues and fluids in the body without causing damages, e.g. by an immunological reaction or other form of inflammation.

The encapsulation material should also be chosen so as to be compatible with the electrolyte and the ions contained therein, i.e. be inert in relation to the compounds, ions and molecules present in the electrolyte. The encapsulation material should further be suitable for storage and transportation, i.e. be able to protect the electrode and/or ion conductor enclosed therein, in addition to the ability to store the electrolyte.

The encapsulation material may, in some applications, further be suitable for long-time insertion in a body, i.e. not be susceptible to degradation by the biochemical environment, such as body fluids and compounds and substances excreted by cells and/or organ systems.

According to some applications the device or parts of the device may be fabricated onto a substrate. The substrate may be electrically and ionically insulating and may comprise rigid materials such as Si wafers with an insulating oxide (SiOx) or nitride layer ($Si_3N_4$), glass wafers such as pyrex wafers, glass substrates, such as microscope slides, plastic substrates such as PET, polystyrene, used in petridishes, and ceramics. The substrates may also be flexible such as plastic films, Orgacon films (both plastic and paper), or paper based materials.

General principles of manufacturing an ion pump device are set forth in EP 1 862 799 A1, and in the documents referred to therein.

The term "active agent" as used in the present disclosure encompasses drugs, genetic materials, and biological materials and can be used interchangeably with "biologically active material" or "therapeutic agent". The term may also encompass any form of the agent, such as a derivative, analog, salt or a prodrug thereof. The agent can be present in various forms, components of molecular complexes and pharmaceutically acceptable salts. However the agent must be in an ionic form, e.g. carry an electrical charge.

The term "agent" can also refer to any pharmaceutical molecules or compounds, therapeutic molecules or compounds, matrix forming molecules or compounds, polymers, synthetic molecules and compounds, natural molecules and compounds, and any combination thereof.

The terms "an effective amount" or "therapeutically effective amount" of an agent, compound or therapeutic, with respect to methods of treatment, refers to an amount of the pharmaceutical, therapeutic, agent or other compound in an preparation which, when administered as part of a desired dosage regimen (at an animal, preferably a human) alleviates a symptom, ameliorates a condition, or slows down the onset of disease conditions according to clinically acceptable standards for the disorder or condition to be treated or the cosmetic purpose. A "therapeutically effective amount" as recognized by those skilled in the art, will be determined on a case by case basis. Factors to be considered include, but are not limited to, the disorder to be treated and the physical characteristics of the patient suffering from the disorder.

In one embodiment, the therapeutic agent is an anti-restenotic agent. In other embodiments, the therapeutic agent inhibits smooth muscle cell proliferation, contraction, migration or hyperactivity. Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), pimecrolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, paclitaxel (as well as its derivatives, conjugates (including polymer deriviatives), analogs or paclitaxel bound to proteins, e.g. Abraxane™) 2'-succinyl-taxol, 2'-succinyl-taxol triethanolamine, 2'-glutaryl-taxol, 2'-glutaryl-taxol triethanolamine salt, 2'O-ester with N-(dimethylaminoethyl) glutamine, 2'-O-ester with N-(dimethylaminoethyl)glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, or its analogs, conjugates (including polymer conjugates) or derivatives. Examples of polymer-drug conjugates are described in J. M. J. Frechet, Functional Polymers: From Plastic electronics to Polymer-Assisted Therapeutics, 30 Prog. Polym. Sci. 844 (2005), herein incorporated by reference in its entirety. In yet another preferred embodiment, the therapeutic agent is an antibiotic such as erythromycin, amphotericin, rapamycin, adriamycin, etc. The term “genetic materials” means DNA or RNA, including, without limitation, of DNA/RNA encoding a useful protein stated below, intended to be inserted into a human body including viral vectors and non-viral vectors. The term “biological materials” include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP’s are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells. Other Non-Genetic Therapeutic Agents Include: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, acetylsalicylic acid, tacrolimus, everolimus, zotarolimus, amlodipine and doxazosin; anti-inflammatory agents such as glucocorticoids, betamethasone, dexamethasone, prednisolone, corticosterone, budesonide, estrogen, sulfasalazine, rosiglitazone, mycophenolic acid and mesalamine; anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives; anesthetic agents such as lidocaine, bupivacaine, and ropivacaine; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides; DNA demethylating drugs such as 5 azacytidine, which is also categorized as a RNA or DNA metabolite that inhibit cell growth and induce apoptosis in certain cancer cells; vascular cell growth promoters such as growth factors, vascular endothelial growth factors (VEGF, all types including VEGF-2), growth factor receptors, transcriptional activators, and translational promoters; vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents, vasodilating agents, and agents which interfere with endogenous vasoactive mechanisms; anti-oxidants, such as probucol; antibiotic agents, such as penicillin, cefoxitin, oxacillin, tobranycin, rapamycin (sirolimus); angiogenic substances, such as acidic and basic fibroblast growth factors, estrogen including estradiol (E2), estriol (E3) and 17-beta estradiol; drugs for heart failure, such as digoxin, beta-blockers, angiotensin-converting enzyme (ACE) inhibitors including captopril and enalopril, statins and related compounds; and macrolides such as sirolimus or everolimus. Preferred biological materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, paclitaxel conjugates and mixtures thereof). For example, derivatives suitable for use in the present disclosure include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, paclitaxel 2-N-methylpyridinium mesylate, and 2'-O-ester with N-(dimethylaminoethyl)glutamide hydrochloride salt. Paclitaxel conjugates suitable for use in the present disclosure include, paclitaxel conjugated with docosahexanoic acid (DHA), paclitaxel conjugated with a polyglutimate (PG) polymer and paclitaxel poliglumex. Other suitable therapeutic agents include tacrolimus; halofuginone; inhibitors of HSP90 heat shock proteins such as geldanamycin; microtubule stabilizing agents such as epothilone D; phosphodiesterase inhibitors such as oliostazole; Barket inhibitors; phospholamban inhibitors; and Serca 2 gene/proteins. Other preferred therapeutic agents include nitroglycerin, nitrous oxides, nitric oxides, aspirins, digitalis, estrogen derivatives such as estradiol, glycosides, tacrolimus, pimecrolimus and zotarolimus. In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration. In certain embodiments, the therapeutic agents for use in the medical devices of the present disclosure can be synthesized by methods well known to one skilled in the art. Alternatively, the therapeutic agents can be purchased from chemical and pharmaceutical companies.

DESCRIPTION OF EMBODIMENTS

Figure 1A:
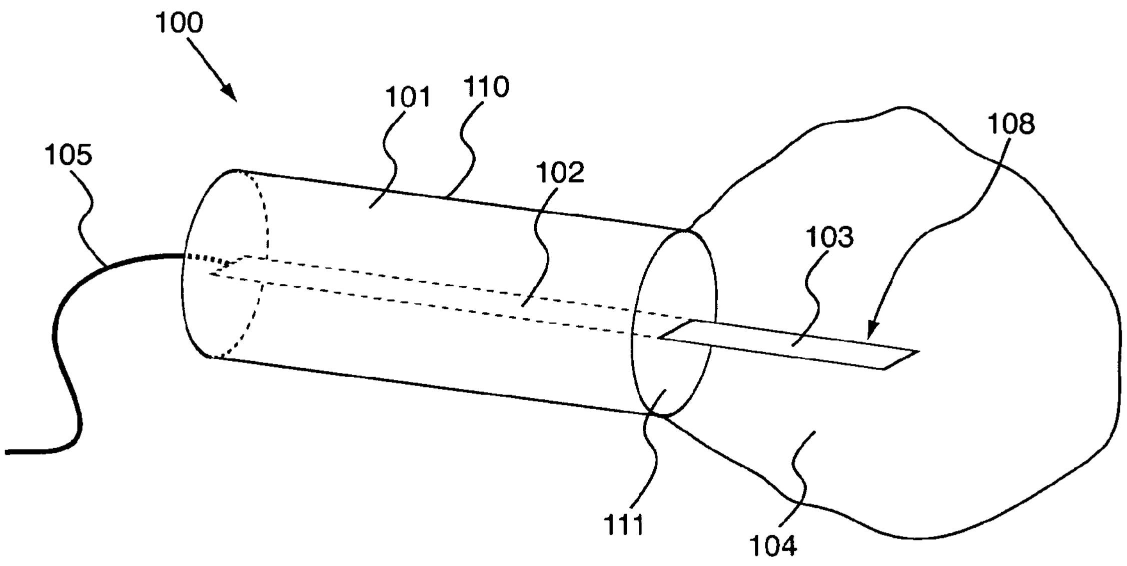
FIG. 1*a* is a schematic perspective view of an ion delivery device.
Figure 1B:
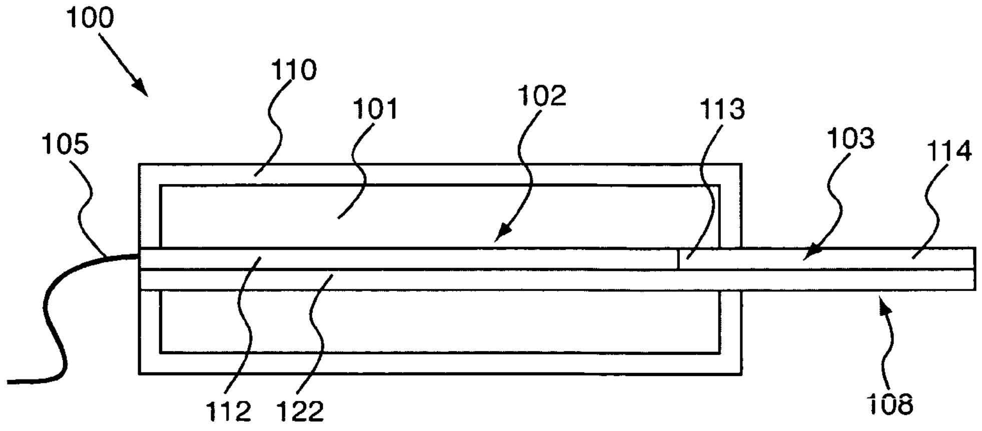
FIG. 1*b* is a schematic cross sectional view of an ion delivery device.

FIGS. 1*a* and 1*b* illustrate an ion delivery device 100. The ion delivery and/or extraction device 100 may essentially be half of the device described in EP 1 862 799 A1, thus comprising a single electrode 102 and an electrolyte 101 and an ion-conducting channel 103, forming an "ion conductor". The electrolyte 101 and electrode 102 may be surrounded by an encapsulation 110. The encapsulated electrolyte 101 may contain the intended delivery molecule in ionic form.

The encapsulation 110 may be formed by an electronically and ionically insulating material, which essentially completely encapsulates the electrolyte. The body of the encapsulation 110 may be formed as a catenoid, a segment of a sphere, a conoid, a right circular or truncated cylinder, i.e. essentially a tube which is sealed at both ends, it may be conical or disc shaped, toroid or serpentine, a square, a rectangle or substantially be shaped according to/adapted for where it is intended to be placed/used.

The electrode 102, may be formed by a redox-active material such as the conducting polymer PEDOT:PSS, as described herein above. The electrode 102 may alternatively be formed by any other material capable of conducting ions and/or electrons, e.g. a metal such as platinum.

The electrode material 112 may be arranged on a substrate 122 (FIG. 1*b*). The substrate may be a flexible material, such as a plastic film or paper.

The ion conductor 103 may be arranged in ionic contact with the electrode 102. By ionic contact is mean that when a first and a second material are in ionic contact a substantial amount of ions comprised in the first material can move from the first material to the second material, possibly via a third material. The ionic movement may be caused by diffusion or by an applied electric field. The ion conductor 103 may be of the same material as the electrode 102. The ion conductor 103 may be formed as a protrusion 108, protruding from one face 111 of the encapsulation 110, which face 111 faces the outside of the encapsulation 104 or "target region". The ion conductor may allow for ions to be transported out of the source electrolyte into the outside 104.

Any number of ion conductors 103 may protrude from, or open at, any number of faces of the encapsulation. The number of ion conductors will be dependent on the application.

The target region may comprise any physiological electrolyte (such as blood or other bodily fluids), or an additional electrolyte incorporated into and/or onto the device, e.g. a hydrogel arranged on the ion-conducting channel 103.

The spatial limitation of the target region is dependent on the application and the area which contacts the ion conductor. For instance if a hydrogel is applied on the ion conductor, the volume of the target region may be limited to the extent of the hydrogel. If the ion conductor is inserted into the blood stream, the target region may be all the blood that flows past and contacts ion conductor.

FIG. 1*b* further illustrates a schematic cross section of a device 100 in which the electrode material 112 may be arranged on a substrate 122. The ion conductor material 115 may further be arranged on the same substrate 122. The ion conductor 103 may, according to one embodiment and as shown in FIG. 1*b*, be arranged such that a first portion 113 is arranged inside the encapsulation 110 and in contact with the first electrolyte 101 and the first electrode 102, and a second portion 114 may be arranged on the outside of the encapsulation, thereby forming a protrusion 108, and in contact with the target area 104.

The device 100 may be connected to electrical control devices (not shown). The connection may be a wire or cable 105 (see e.g. FIGS. 1*a*, 1*b* and 2).

In order to facilitate the operation of the device a closed electro-chemical circuit may be provided.

Figure 2:
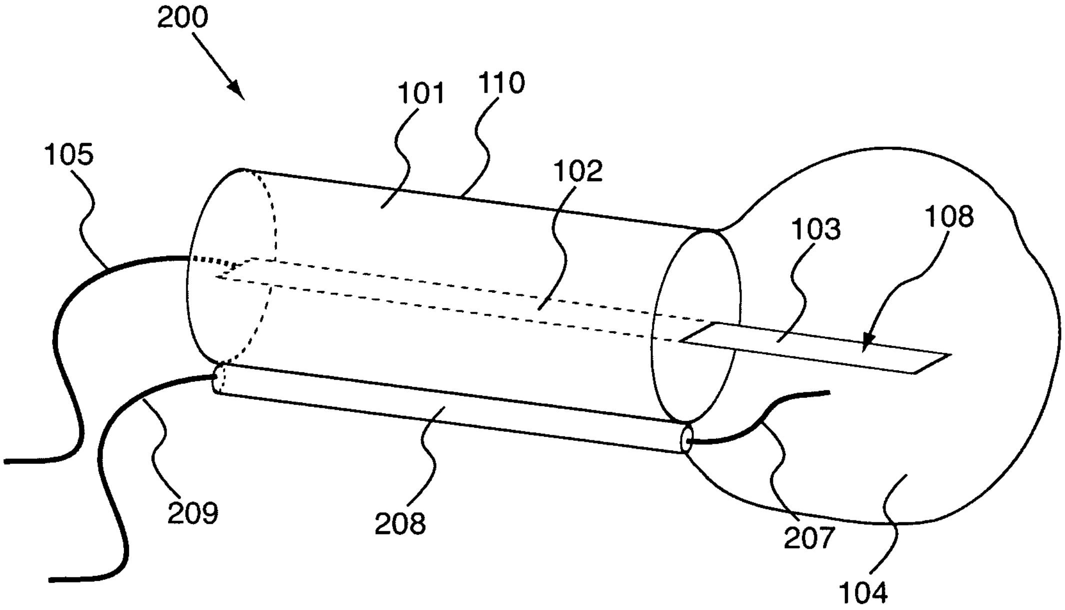
FIG. 2 is a schematic perspective view of an ion delivery device provided with a counter electrode.

FIG. 2 is a schematic perspective view of an ion delivery device provided with a counter electrode 207. A counter-electrode may be used to complete the electrochemical circuit and thus enable the electrochemical reaction which drives the flow of ions from/to the encapsulated electrolyte 101.

In order for the counter electrode to close the electro-chemical circuit it must be in ionic contact with the target region 104.

A simple counter-electrode may be a metal-wire 207 which may be in contact with the target area 104. FIG. 2 illustrates a wire 207, which may be electrically insulated 208 and attached to the device 200. The wire may be connected to an electronic control system by the connection 209. The connection may be a wire or cable. Voltage may be supplied between the two electrical conductors 105 and 209.

The counter-electrode may further have the geometry of a mesh, a grid, a plate, a film. The counter-electrode may be a metal or any other electrically conductive material, or any of the materials described above for the electrodes.

The counter electrode 207 does not, according to one embodiment, need to be attached to the device (not shown).

However the counter-electrode must be in ionic contact with the same target region 104 as the ion-conductor 103.

In this situation, the voltage supplied causes ions to be transported from the first electrolyte 101, to the electrode 102 and/or ion conductor 103, and from the ion conductor to the outside 104 (or target area).

Electrical current is sustained by electrochemical reactions at the metal wire 207 which cause electrons to be withdrawn from the metal into the target area 104 (for transport of cations out of the ion pump).

The ion delivery and/or extraction device may be operated by applying a voltage between the first electrode 102 and the counter electrode 207. The applied voltage drives redox reactions at the electrodes 102, 207. In the case of a positive voltage between the first electrode 102 and counter electrode 207, i.e. using the first electrode 102 as the anode and counter electrode 207 as the cathode, the first electrode 102 may be oxidized and the counter electrode 207 may be reduced. In the case of a negative voltage between the first electrode 102 and counter electrode 207, i.e. using the first electrode 102 as the cathode and counter electrode 207 as the anode, the first electrode 102 may be reduced and the counter electrode 207 may be oxidized. As a non-limiting example, utilizing a positive voltage (first electrode as anode) and PEDOT:PSS as electrode material, the chemical reaction at the first electrode, may be represented as ($M^+$ is a mobile cation):

First electrode: $PEDOT^0 + M^+PSS^- \rightarrow PEDOT^+PSS^- + M^+ + e^-$

A reduction reaction, not shown in the scheme, may occur at the counter-electrode to complete the electrical circuit, which is readily understood by a person skilled in the art.

As can be understood from the reaction scheme, the reactions require that an electron is transferred from the first electrode 102 to the counter electrode 207 at the same time as a cation is transferred through the ion conductor 103 from the first electrode 101 to the target region 104. Once the ions reach the target region 104 they may diffuse or by other means reach the counter electrode 207. The ionic species that actually reach the counter-electrode in order to close the electric circuit may be the same as the ionic species leaving the ion conductor, or it may be different, e.g such ions as are present in the target region, for example sodium ions, which are usually present in body fluids and cells. This is the mechanism behind the ion transport in the device. If anions are pumped through the ion channel instead of cations, the reaction scheme is similar and the relationship between electrical current and transported ions holds. The rate at which ions are transported through the ion channel may be approximately proportional to the voltage applied between the source and target electrodes in the range of typical voltages 0-20 V. An inherent advantage of a device according to the present disclosure which utilizes conducting polymers is the low voltage required to effect ion transport from a source to a target electrolyte.

One possible drawback of this embodiment is that this chemical reduction process may in some instances cause undesirable—even toxic—by-products.

An alternative embodiment may therefore incorporate a conducting-polymer counter-electrode, which would eliminate or reduce the risk of undesirable by-products being formed.

Figure 3A:
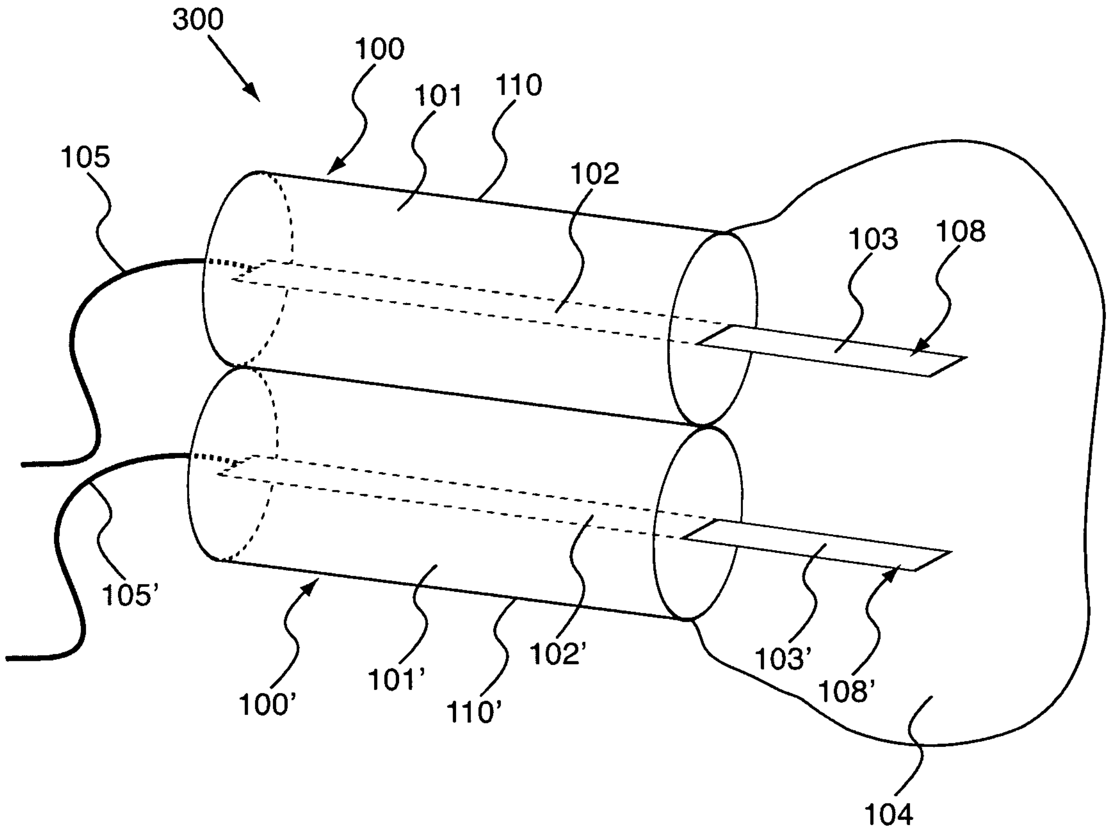
FIG. 3 is a schematic perspective view of an ion delivery device with two ion conductors.

FIG. 3 illustrates an ion delivery device 300 with a first 100 and second 100' device arranged in connection with each other. The first device 100 may comprise the source electrolyte 101 and the source electrode 102 and a first ion conductor 103, arranged to deliver and/or extract ions from a target region 104 outside the encapsulation 110. The second device 100' may hence constitute the counter-electrode, where the second ion conductor 103' is in contact with the same target region 104 as the first ion conductor 103.

According to this alternative embodiment, the ion pump may be operated by applying a voltage between the source electrode 102 and the counter electrode 102'. The applied voltage drives redox reactions at the electrodes 102, 102'. In the case of a positive voltage between the first electrode 102 and counter electrode 102', i.e. using the first electrode 102 as the anode and counter electrode 102' as the cathode, the first electrode 102 may be oxidized and the counter electrode 102' may be reduced. In the case of a negative voltage between the first electrode 102 and counter electrode 102', i.e. using the first electrode 102 as the cathode and counter electrode 102' as the anode, the first electrode 102 may be reduced and the counter electrode 102' may be oxidized. As a non-limiting example, utilizing a positive voltage (first electrode as anode) and PEDOT:PSS as electrode material, the chemical reaction may be represented as:

First electrode: $PEDOT^0 + M_1^+PSS^- \rightarrow PEDOT^+PSS^- + M_1^+ + e^-$

Counter electrode: $PEDOT^+PSS^- + M_2^+ + e^- \rightarrow PEDOT^0 + M_2^+PSS^-$ wherein $M_1^+$ and $M_2^+$ are mobile cations. $M_1^+$ and $M_2^+$ may be the same ionic species. $M_1^+$ and $M_2^+$ may also be different ionic species, $M_2^+$ may for instance be an ionic species present in the target region, e.g. sodium ions, which are usually present in body fluids and cells.

As can be seen from the reaction scheme, the reactions require that an electron is transferred from the first electrode 102 to the counter electrode 102' at the same time as a cation is transferred through the ion conductor 103 from the first electrode 101 to the target region 104. Once the ions reach the target region 104 they may diffuse or by other means reach the counter electrode 102', by passing trough the ion conductor 103'. This is the mechanism behind the ion transport in the device. If anions are pumped through the ion channel instead of cations, the reaction scheme is similar and the relationship between electrical current and transported ions holds. The rate limiting process is ion transport since electrons are more easily transported. The rate at which ions are transported through the ion channel may be approximately proportional to the voltage applied between the source and target electrodes in the range of typical voltages 0-20 V. An inherent advantage of a device according to the present disclosure which utilizes conducting polymers is the low voltage required to effect ion transport from a source to a target electrolyte.

The two encapsulated electrolyte devices 100, 100' may be of identical geometry, or they may be different (i.e., one may be a tube with a strip as ion conductor, and the other may be rectangular with a plug-shaped ion-conducting region). Likewise, the materials used to fabricate the two halves 100, 100' may or may not be the same. The electrolytes used in both halves 100, 100' may or may not be the same, all depending on the application.

An alternative embodiment, which is not shown in the figures, of the device 300 shown in FIG. 3, may be that a counter-electrode, such as the one shown in FIG. 2 is attached to the device 300. Thereby both devices 100 and 100' may function as source electrodes/electrolytes. The counter-electrode may be the same as described above for 207.

Figure 4:
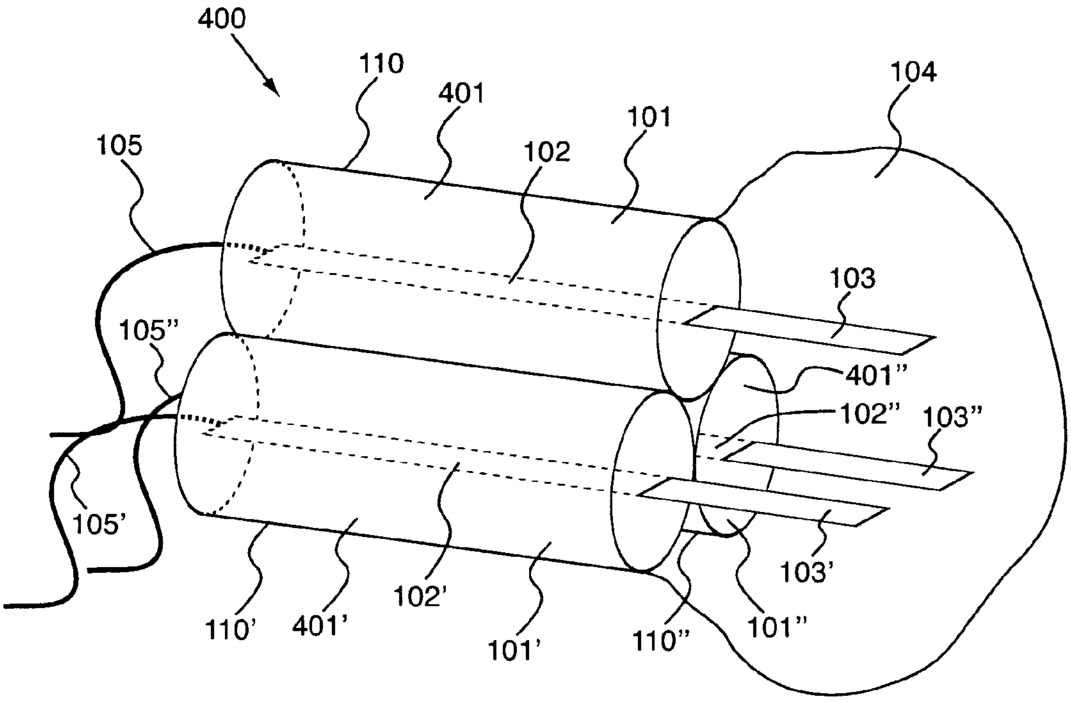
FIG. 4 is a schematic perspective view of an ion delivery device with multiple ion conductors.

FIG. 4 is a schematic perspective view of an ion delivery device 400 with multiple ion delivery and/or receiving devices, i.e. 401, 401', 401". In such a system, more than one source and/or receiving electrolyte 401, 401', 401" may deliver to and/or receive from the same target region, outside of the encapsulations 110, 110' and 110". According to one embodiment two of the ion delivering (and/or receiving) devices 401, 401' may contain ions to be delivered, while a third device 401" may be used as counter-electrode.

According to yet an alternative all three, or more, devices 401, 401', 401", may be used to deliver ions to the target region 104, where an additional (not shown) counter-electrode, may be provided for closing the electrochemical circuit.

The additional counter electrode may be a device such as 100 (FIG. 1*a*) or a wire such as 207 (FIG. 2).

The devices 401, 400', 401" may be connected to at least one electronic control device. The electrical connection may be wires 105, 105', 105" connected to the devices 401, 401', 401" respectively.

Application of various voltages between the three electrical connections 105, 105', 105" may determine the ratio of delivery from the each of the source systems 401, 401', 401".

The ion delivery and/or receiving devices 400, 401', 401" may, according to one embodiment, be attached to each other.

According to an alternative embodiment the devices may be separated.

Figure 5:
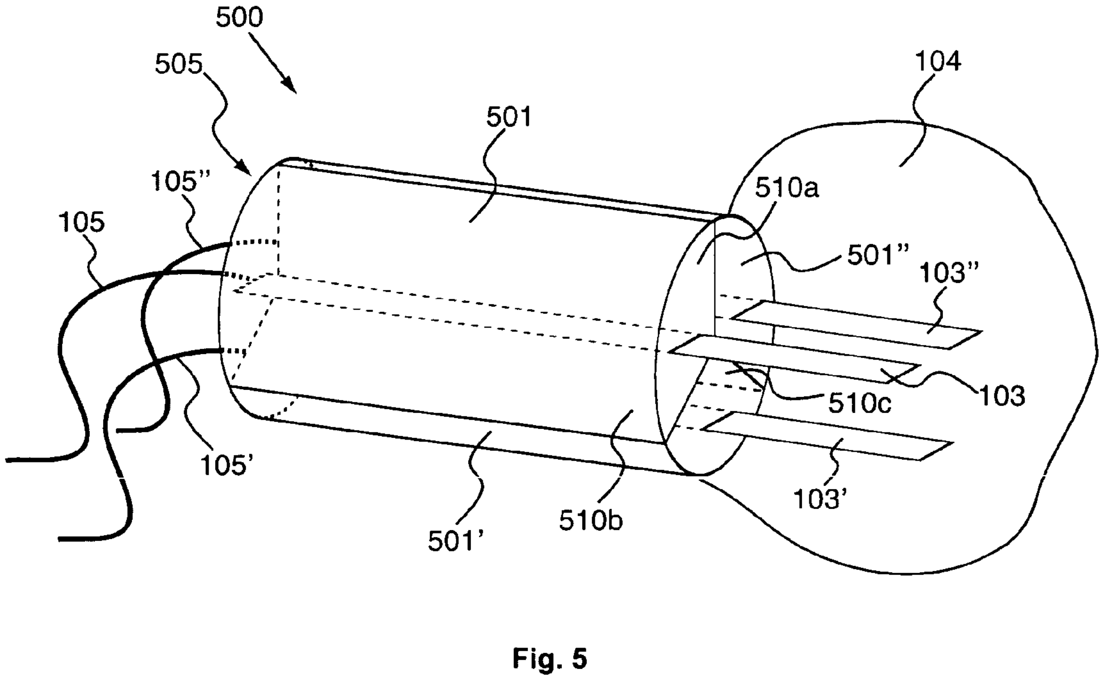
FIG. 5 is a schematic perspective view of an ion delivery device with multiple ion conductors.

FIG. 5 illustrates an ion delivery and/or receiving device 500, with multiple electrolyte/electrode devices 501, 501', 501".

The electrolyte/electrode devices may, according to this embodiment, be attached or packaged as a multi-lumen or multi-chamber structure, which may be used in place of, or as a complement to, the separate systems shown in the previous FIGS. 3 and 4.

Each of the chambers 501, 501', 501" may, according to one embodiment comprise an electrolyte 101, an electrode 102 and an ion conductor 103. Hence chamber 501 may comprise a first electrolyte 101, a first electrode 102 and a first ion conductor 103; chamber 501' may comprise a second electrolyte 101', a second electrode 102' and a second ion conductor 103' etc.

Each of the devices may also be connected to electrical control devices, by the connections 105, 105', 105".

Figure 6:
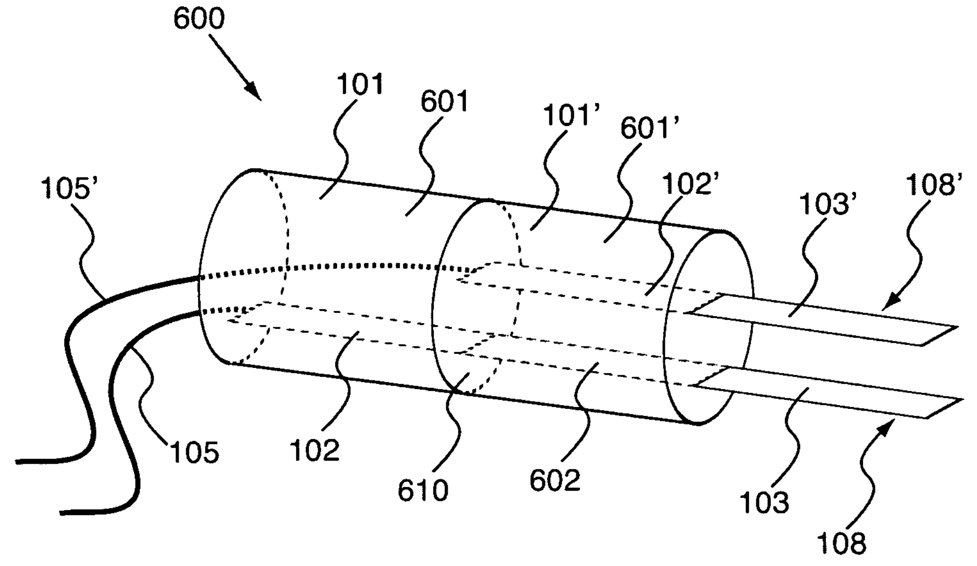
FIG. 6 is a schematic perspective view of an ion delivery device with two ion conductors.

In the device of FIG. 6, the multiple chambers are shown as lumina of a single enclosure 505, divided by dividers 510*a*, 510*b*, 510*c*.

The enclosure 505 may be a tube as shown in FIG. 5, but may also be any other geometrical configuration providing the same functionality.

The number of lumina or chambers present in one enclosure 505 may range from one, i.e. a device identical to the FIG. 1*a* device 100, to any number of lumina or chambers, limited only by the application.

One of the electrode/electrolyte devices 501, 501', 501", may act as a counter-electrode.

According to one alternative three devices 501, 501', 501", may be used to deliver ions to the target region 104, where an additional (not shown) counter-electrode, may be provided for closing the electrochemical circuit.

The additional counter electrode may be a device such as 100 (FIG. 1*a*) or a wire such as 207 (FIG. 2).

FIG. 6 illustrates an alternative embodiment of the multichamber device. The device 600 may, according to this embodiment, comprise a first 601 and second 601' chamber arranged in a co-axial relation to each other. The chambers may be divided by an inner wall 610. The inner wall 610 may be both ionically and electrically insulating. The inner wall 610 may further be impermeable, i.e. does not allow for any physical transport of molecules from one electrolyte to the other. The first chamber 601 may comprise a first electrolyte 101 and a first electrode 102. The second chamber 601' may comprise a second electrolyte 101', which may be the same as, or different from, the first electrolyte. The second chamber may further comprise a second electrode 102', which may be connected to a second ion conductor 103', which may protrude from one face of the device 600. The first electrode 102 may pass through the ionically and electrically insulating inner wall 610 and extend further through the second electrolyte, and finally be connected to an ion conductor 103, which may protrude from one face of the device 600. The portion of the first electrolyte 102 that extends through the second electrolyte 101' may be ionically insulated 602, in order to prevent the electrochemical circuit to be closed within the second chamber.

The insulation 602 may be a silicone film, but may also be any other insulation providing ionic insulation. By the insulation 602, the ions may be transported from the first electrolyte 101 to the first electrode and through the second electrolyte to the ion conductor 103 and finally be released on the outside of the encapsulation, or the target region (reference numeral 104, shown in FIG. 1*a*), when a voltage is applied over the electrodes and hence creating a potential difference which drives the transport of ions.

According to one alternative the first and second electrodes 102, 102' and electrolytes 101, 101', respectively, may act as ion delivery and/or receiving devices and an additional or separate counter electrode may be utilised to drive the transport of ions (not shown).

The devices 601 and 601' may be connected to electronic control devices. The electrical connection may be wires 105, 105' connected to the devices 601, 601' respectively.

Application of various voltages between the two electrical connections 105, 105' may determine the ratio and/or sequential of delivery from the each of the source systems 601, 601'.

Figure 7:
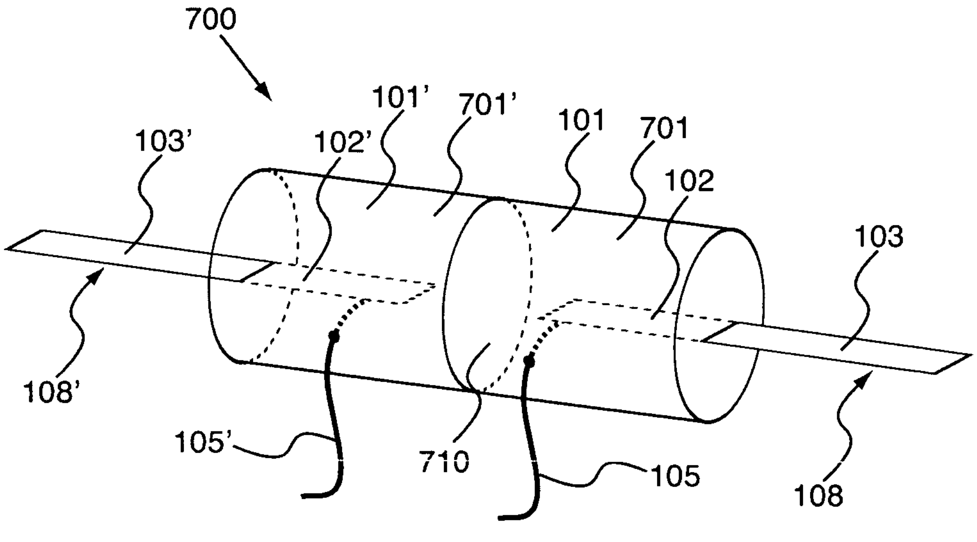
FIG. 7 is a schematic perspective view of an ion delivery device with two ion conductors.

FIG. 7 illustrates an alternative embodiment of the device shown in FIG. 6. The device 700 according to this embodiment may comprise a first chamber 701 and a second chamber 701'. The chambers may be divided by a wall 710. The inner wall 710 may be both ionically and electrically insulating. The inner wall 710 may further be impermeable, i.e. does not allow for any physical transport of molecules from one electrolyte to the other.

The first chamber 701 may comprise a first electrolyte 101 and a first electrode 102, which may be connected to a first ion conductor 103. The second chamber 701' may comprise a second electrolyte 101' and a second electrode 102', which may be connected to a second ion conductor 103'.

The ion conductors 103 and 103' may, according to this embodiment, protrude from different faces of the device

700. The ion conductors may, according to one embodiment, protrude from opposite sides of the device 700.

According to one alternative the first and second electrodes 102, 102' and electrolytes 101, 101', respectively, may act as ion delivery and/or receiving devices and an additional or separate counter electrode may be utilised to drive the transport of ions (not shown).

The devices 701 and 701' may be connected to electronic control devices.

The electrical connection may be wires 105, 105' connected to the devices 701, 701' respectively.

The devices 701 and 701' may be connected to electronic control devices. The electrical connection may be wires 105, 105' connected to the devices 701, 701' respectively.

Application of various voltages between the two electrical connections 105, 105' may determine the ratio of and/or sequential delivery from each of the source systems 701, 701'.

According to the figures referred to above, the electrodes and ion conductors have been depicted as strip-shaped geometries, it shall however be noted that the electrodes and ion conductors may have any other suitable shape or geometry.

The encapsulations or chambers as illustrated in the figures may also have any geometrical shape or configuration suitable for the application. In the below a few alternative embodiments of ion conductor and/or electrode geometries and designs will be described, it shall however be noted that this description is in no way limiting to the possible design or shape of the ion conductors and/or electrodes according to the present solution.

FIGS. 8*a*-8*f* illustrate alternative embodiments of delivery portions of ion conductors. Herein below "ion conductor" is meant as a comprehensive term referring to the protrusion 108.

Figure 8A:
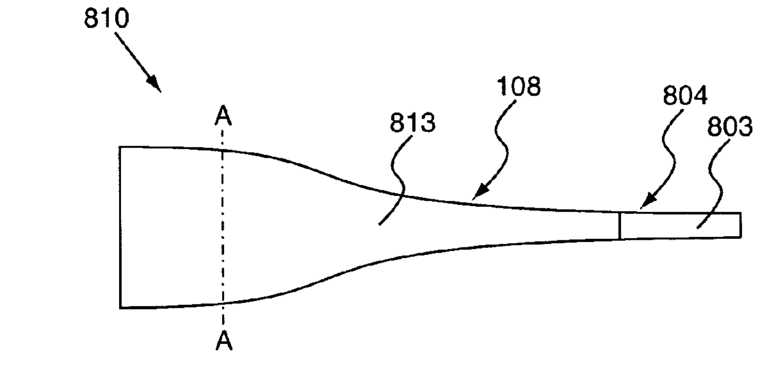
FIGS. 8*a*-8*f* schematically illustrate alternative embodiments of delivery portions of ion conductors.
Figure 8B:
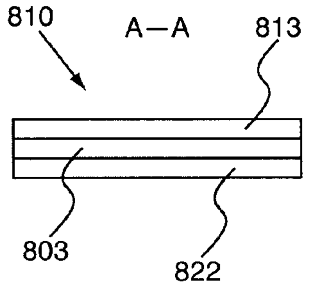

FIG. 8*a* illustrates one embodiment of an ion conductor 810, and FIG. 8*b* is a cross-section along the line A-A of FIG. 8*a*. The ion conductor 810 may be tapered. The ion conductive channel 803 may be formed by an electrochemically active material, such as PEDOT:PSS, which may be arranged on a substrate 822, such as a plastic foil. The ion conductive channel 803 may further be provided with an insulation material 813. The insulation material may for instance be SU-8 or silicone glue. By the provision of the insulation material there may be provided a way of preventing the release of ions until the end 804 of the ion conductive channel 803.

Figure 8C:
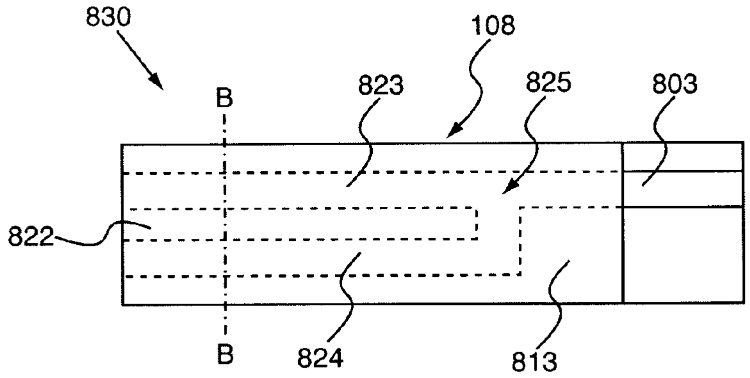
Figure 8D:
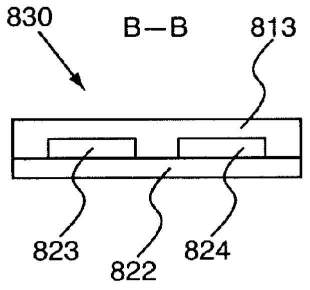
Figure 8E:
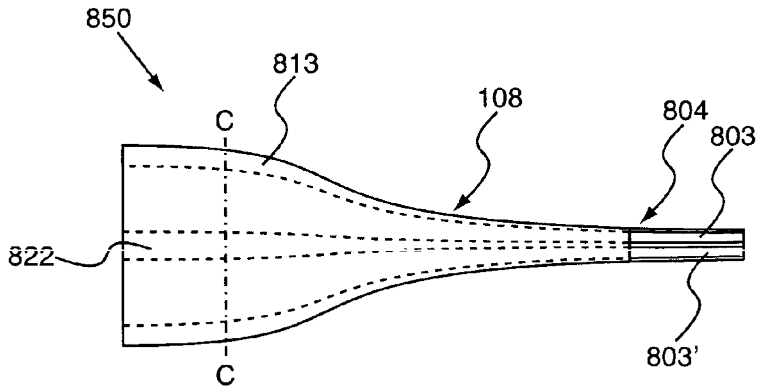

FIG. 8*c* illustrate one embodiment of an ion conductor 830. FIG. 8*d* illustrate a cross-section along the line B-B of FIG. 8*c*. The ion conductor 830 may be provided with two ion conductive channels 823 and 824. The channels 823 and 824 may be merged together at a junction 825 into a common channel 803. An insulation material 813 may be arranged to surround the channels 823 and 824, to ensure ion release at specific areas of the ion conductor 830. The ion channels may be arranged on a substrate 822.

The ion conductive channels 823 and 824 may be connected to (not shown) different sources, i.e. different electrodes 102, 102'.

The ion conductive channel 824 may, according to one embodiment, be a waste channel leading to a waste electrolyte system and the channel 823 may be a delivery channel leading from a source electrode/electrolyte system.

By applying a potential difference over the source and waste system, i.e. pumping ions from the source system to the waste system, the channels 823 and 824 may be filled with ions. By switching the circuit, ions may be delivered from the filled ion channel 823 to the channel 803 and finally to the outside of the encapsulation or target region (not shown).

Hence, according to one embodiment, the junction 825 between the channel 823 and the waste channel 824 may be pre-filled, or pre-loaded, with ions. The junction 825 thus functions as a pre-loading region for ions. By filling the junction 825 with ions it may be possible to exactly dosage the ions to be delivered, since the junction channel 825 may be formed as a well-defined region capable of holding a predetermined amount of ions.

A faster response, i.e. a faster delivery of ions from the ion conductor to the outside, may also be achieved by the pre-loading of ions into the junction 825, since the junction 825 may be placed at a short distance from the end 804, i.e. the delivery region, of the ion conductive channel 803. The waste ion channel/electrode hence allows an improved temporal control of ion delivery, since the ion conductive channel may be partially or fully filled with the ion to be transported by transporting the ion to the waste electrolyte before the actual ion transport to the target region is initiated.

Figure 8F:
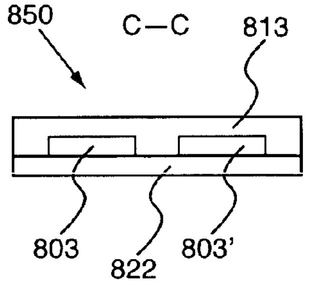

FIG. 9*e* illustrates one embodiment of an ion conductor 850. FIG. 8*f* is a cross-section along the line C-C of FIG. 8*e*. The ion conductor 850 may comprise two or more ion conductive channels 803, 803' separated by an insulation material 813, such as SU-8 or a silicone glue. The ion conductive materials may be formed by an electrochemically active material, such as PEDOT:PSS.

The ion conductive channels 803, 803' may further be arranged on a support material 822, such as plastic or paper foil.

The ion conductive channels may be connected to (not shown) two or more source electrodes 102, 102', which may be different from each other.

The channels 803, 803' may, according to one alternative be separated throughout the entire length of the ion conductor 850, and may hence be able to release ions at spatially separated areas at the end 804 of the ion conductor 850. This may allow for a very well defined delivery and/or extraction of ions to/from the target region (see FIG. 1*a*, reference numeral 104).

The ion conductor 850 may, according to one alternative, further be tapered.

Figure 9:
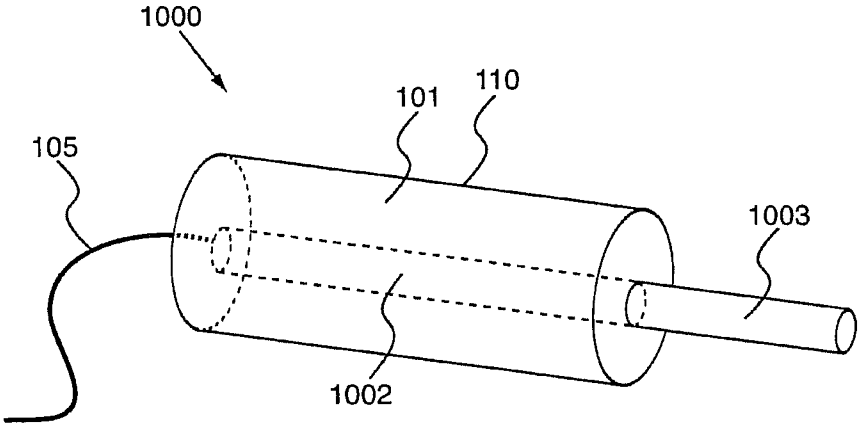
FIG. 9 is a schematic perspective view of an ion delivery device with a tubular delivery portion.

FIG. 9 illustrates yet an alternative embodiment of the ion delivering and/or receiving device. The device 1000 may comprise an electrode 1002, and an ion conductor 1003 having substantially constant circular cross-sections. The electrode and ion conductor may hence be substantially tubular. The electrode and ion conductor may also have any other substantially non-planar cross-section.

The ion conductor and/or electrode may be formed of a wire, or tube or fibre, which may be coated with e.g. an electrochemically active material such as PEDOT:PSS. The wire, tube or fibre may hence be a supporting substrate, such as a plastic rod or tube. The ion conductor may further be over oxidized or insulated with an insulation material, such as SU-8 or a silicone glue.

The ion conductor 1003 may, according to one, not shown, embodiment, have a circular cross-section of varying dimensions, such that a portion of the ion conductive channel may have an increased cross-section. This increased cross-sectional portion may allow for ions to be pre-loaded into the ion conductive channel. The portion having an increased cross-section may be designed specifically to be able to retain a certain amount of ions. The ion conductive channel may be provided with any number of such increased cross-sectional portions, i.e. any number of pre-loading areas.

The pre-loading areas may also be realized in an ion conductor having a cross-section which is rectangular or square, or of any other suitable geometry.

The ion conductor and/or electrode may also have a conical shape, i.e. be tapered.

Figure 10A:
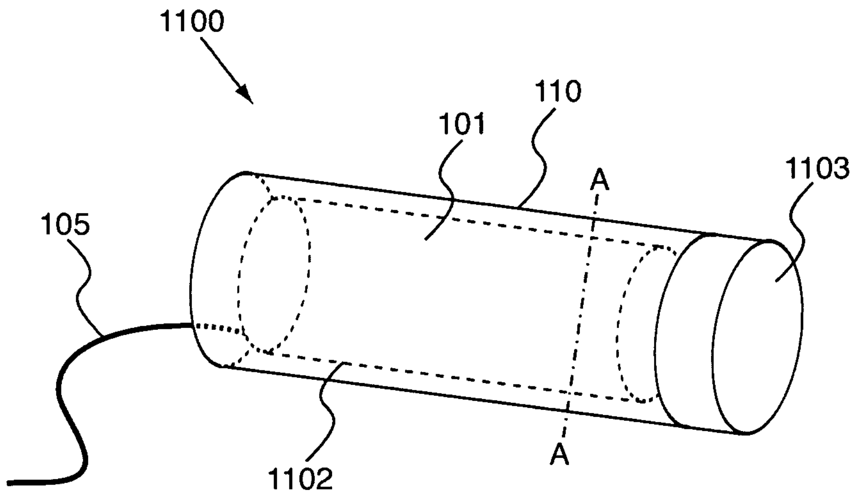
FIGS. 10*a*-10*b* is a schematic perspective view, and a schematic sectional view, respectively, of an ion delivery device having an alternative delivery portion.
Figure 10B:
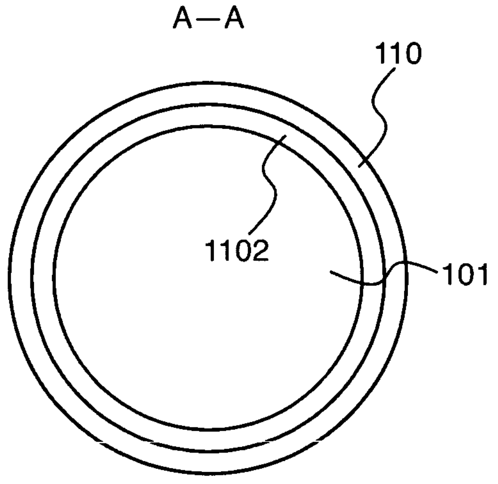

FIGS. 10*a* and 10*b* illustrates a device 1100 in which the electrode 1102 may be coated onto the internal surface 1110 of the encapsulation 110. The ion conductor 1103 may be formed as a plug arranged at the end of the encapsulation.

Figure 11:
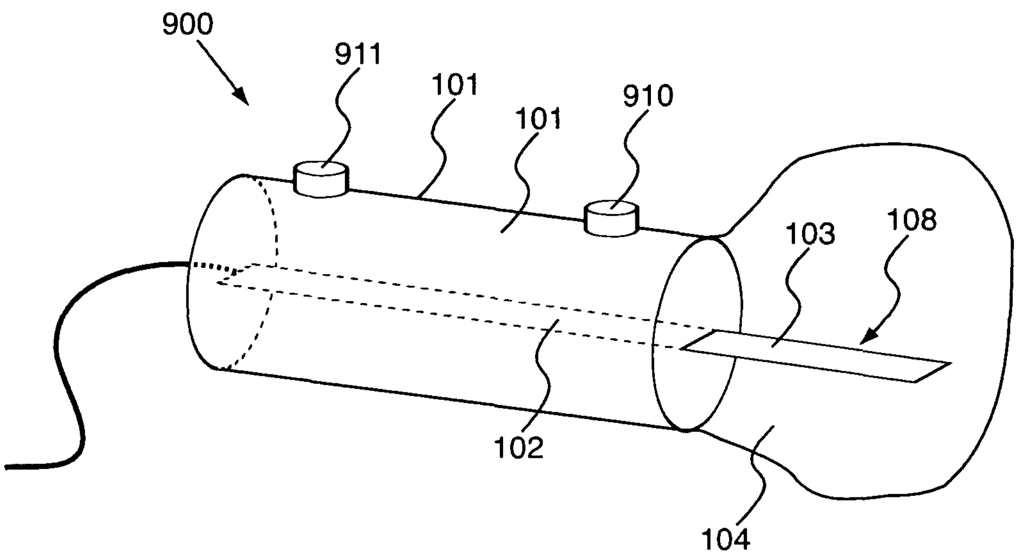
FIG. 11 is a schematic perspective view of a refillable ion delivery device.

FIG. 11 illustrates an ion delivery and/or receiving device 900, which may comprise at least one region through which the inside of the encapsulation may be accessed. This may, for instance, be advantageous for refill or extraction of the electrolyte 101.

The regions may be integrated with the encapsulation material. The region may be a port, a connector, a self-healing membrane, a valve etc. or any other device suitable for this application.

The device 900 may, according to one embodiment, comprise two regions 910 and 911 placed at spaced apart portions of the device 900. For example, one of the regions may be used for ventilation of gas trapped inside the encapsulation 110 and the other may be used for refilling electrolyte into the encapsulation.

Figure 12:
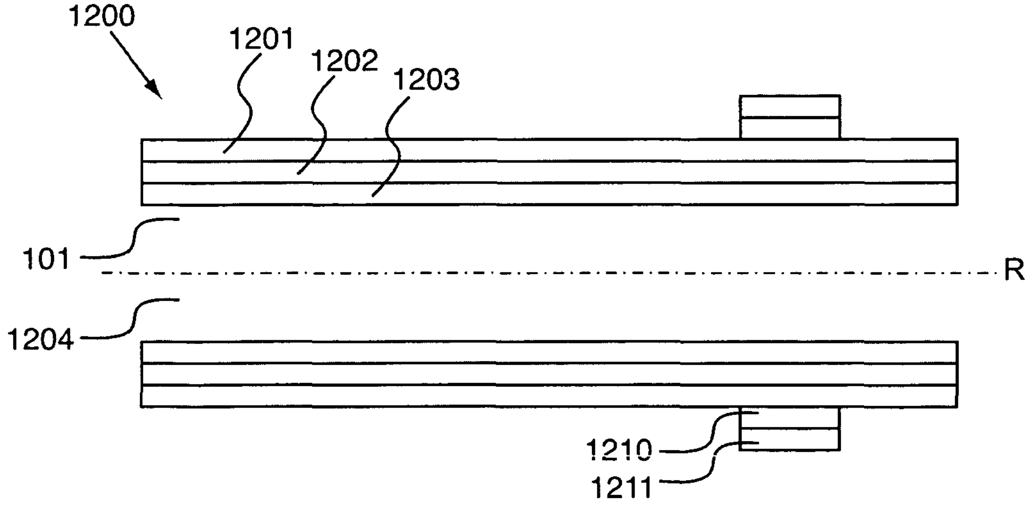
FIG. 12 is a schematic sectional view of a tubular ion delivery device.

FIG. 12 illustrates a cross section of one embodiment of an ion delivery and/receiving device 1200. The device 1200 may have a multi-walled configuration. The outer wall 1201 may be the ion conductor.

The wall 1202 may comprise the electrode material. The electrode-wall 1202 may be ionically and electrically conducting. The electrode may be formed by an electrochemically active material, such as PEDOT:PSS.

The wall 1203 may be formed of a support, which may optionally be integrated in the device 1200. The support wall 1203 may be formed by a material which is electrically insulating, but has a low ionic resistance, such as a plastic mesh tube.

The inner space 1204 may be filled with the electrolyte 101.

The connection to an electrical control device may be made at the wall 1202 (not shown).

A counter-electrode 1211 may, according to one embodiment, be arranged on the outside of the ion conductor wall 1202. The counter electrode may be separated from the ion conductor wall by an insulating layer 1210.

The counter-electrode may, according to one alternative, be arranged separately from the device 1200. The counter electrode may comprise a device, as shown in FIG. 1*a*; or a wire, as shown in FIG. 2.

By applying a potential difference over the electrode wall 1202 and the counter electrode, ions may flow from the electrolyte 101, through the (optional) wall 1203, the electrode wall 1202 and the ion conductor wall 1201 out into the outside (not shown) of the device 1200.

The device 1200 may, but need not, be substantially tubular.

Figure 13:
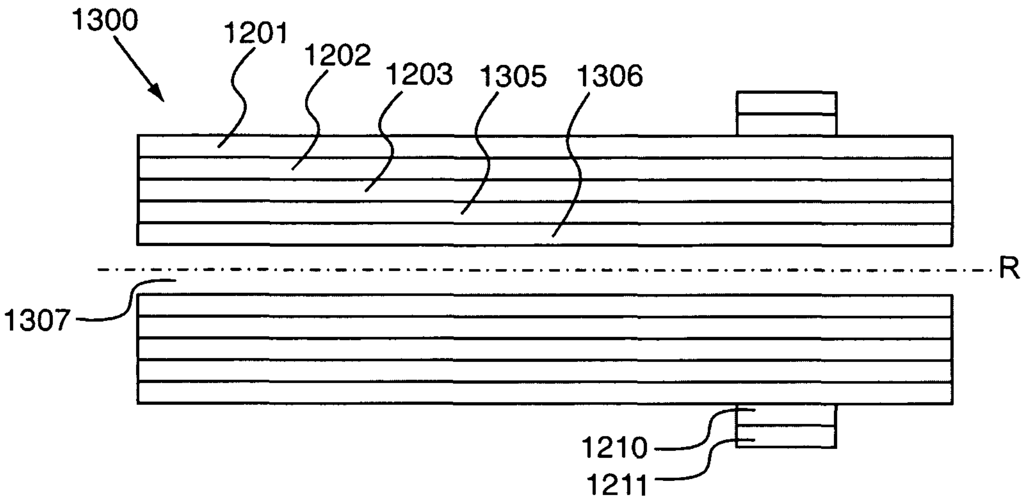
FIG. 13 is a schematic sectional view of a tubular ion delivery device having a longitudinal through channel.

FIG. 13 illustrates an alternative embodiment of the device shown in FIG. 12. The outer wall 1201 may be the ion conductor.

The wall 1202 may comprise the electrode material. The electrode-wall 1202 may be ionically and electrically conducting. The electrode may be formed by an electrochemically active material, such as PEDOT:PSS.

The wall 1203 may be formed of a support material, which may optionally be integrated in the device 1200. The support wall 1203 may be formed by a material which is electrically insulating, but has a low ionic resistance, such as a plastic mesh tube.

The wall 1305 may comprise the electrolyte. The electrolyte may be formed in a semi-solid material, such as a gel.

The wall 1306 may optionally be arranged in the device. The wall 1306 may comprise an inner wall of an ionically and electrically insulating material, such as a silicone tubing or a silicone glue.

Along the axis R a substantially hollow inner space 1307 may be formed.

The connection to an electrical control device may be made at the wall 1202 (not shown).

A counter-electrode 1211 may, according to one embodiment, be arranged on the outside of the ion conductor wall 1202. The counter-electrode may be separated from the ion conductor wall by an insulating layer 1210.

The counter-electrode may, according to one alternative, be arranged separately from the device 1300. The counter electrode may comprise a device, as shown in FIG. 1*a*; or a wire, as shown in FIG. 2.

By applying a potential difference over the electrode wall 1202 and the counter electrode, ions may flow from the electrolyte 1305, through the (optional) wall 1203, the electrode wall 1202 and the ion conductor wall 1201 out into the outside (not shown) of the device 1300.

The device 1300 may, but need not, be substantially tubular.

Figure 14:
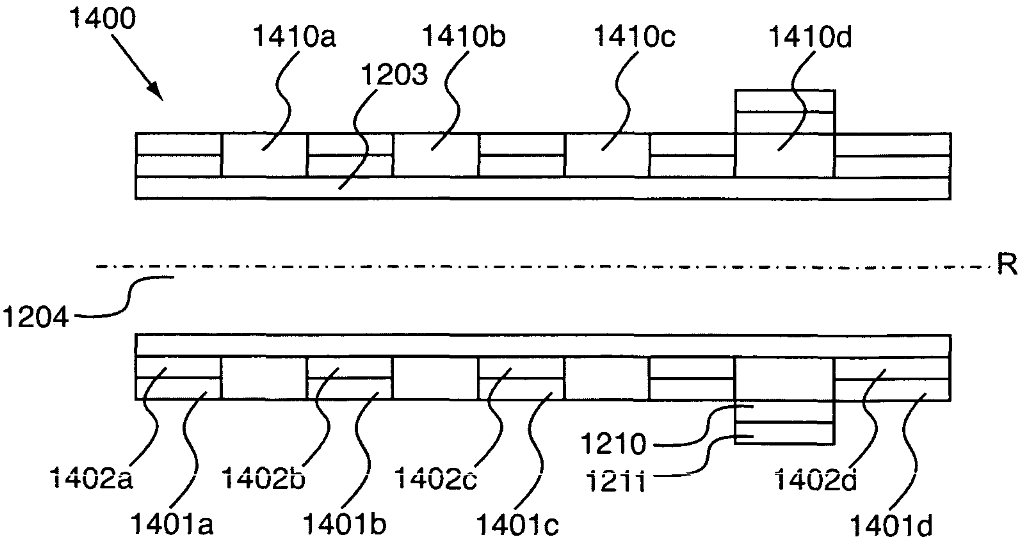
FIG. 14 is a schematic sectional view of a multiple electrode tubular ion delivery device.

FIG. 14 illustrates yet an alternative embodiment of the devices shown in FIGS. 12 and 13. The device 1400 may include regions of insulation material 1410*a*-1410*d*, arranged to form an alternating pattern of insulation material 1410*a*-1410*d* and ion conductor and electrode walls, 1401*a*-1401*d* and 1402*a*-1402*d* respectively. A counter-electrode 1211 may, according to one embodiment, be arranged on the outside of the device 140. The counter-electrode may be separated from the outside wall by an insulating layer 1210. The counter-electrode may, according to one alternative, be arranged separately from the device 1400. The counter electrode may comprise a device, as shown in FIG. 1*a*; or a wire, as shown in FIG. 2.

By applying a potential difference over the electrode walls 1402*a*-1402*d* and the counter electrode, ions may flow from the electrolyte 1204 (or electrolyte wall 1305, not shown), through the (optional) wall 1203, the electrode wall 1402*a*-1402*d* and the ion conductor wall 1401*a*-1401*d* out into the outside (not shown) of the device 1400. The alternating pattern of ion conductor and insulation material on the outside wall may provide delivery and/or extraction of ions at specified locations along the length of the device 1400.

The electrode walls 1402 *a*-1402*d* may also have separate connections to control devices. A spatial control of the delivery may hence be achieved.

The delivery portions 1401*a*-1401*d*/1402*a*-1402*d* may also be arranged to deliver different ionic species.

The device 1400 may be substantially tubular.

Figure 15:
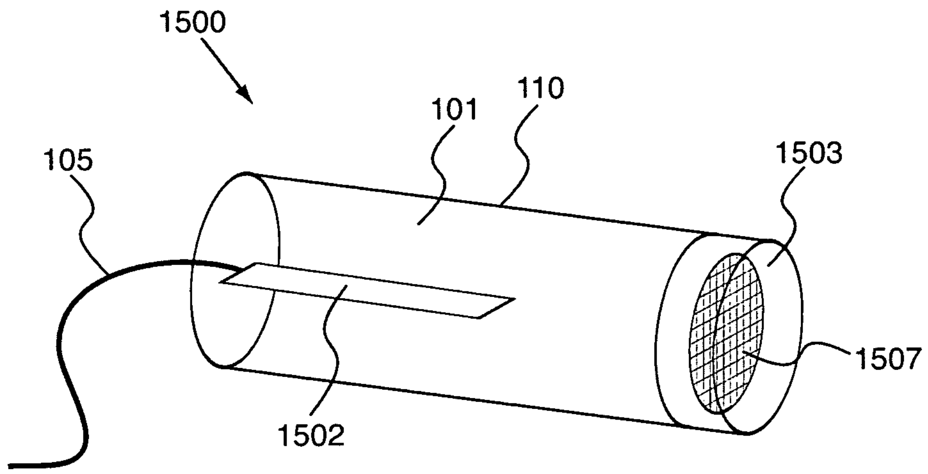
FIG. 15 is a schematic perspective view of an ion delivery device having an integrated counter electrode.

FIG. 15 illustrates an alternative embodiment of the present disclosure. The device 1500 may comprise a first electrode 1502, a first electrolyte 101 encapsulated in the encapsulation 110 and a second electrode 1507 embedded in the ion conductive channel 1503. The second electrode 1507 may be of a highly porous material, e.g. have a mesh like structure. The electrode 1507 may be a metallic mesh.

The electrode 1507 may be a counter-electrode.

The first electrode may be made shorter than the length of the encapsulation, thereby ensuring that no physical contact may be made between the first and second electrode.

When a voltage is applied between the counter-electrode 1507 and the source (first) electrode 1502 ions may be accelerated towards the mesh electrode and thereby transported out of the device 1500 into the outside of the encapsulation (not shown, referring to FIG. 1*a* reference numeral 104).

Figure 16:
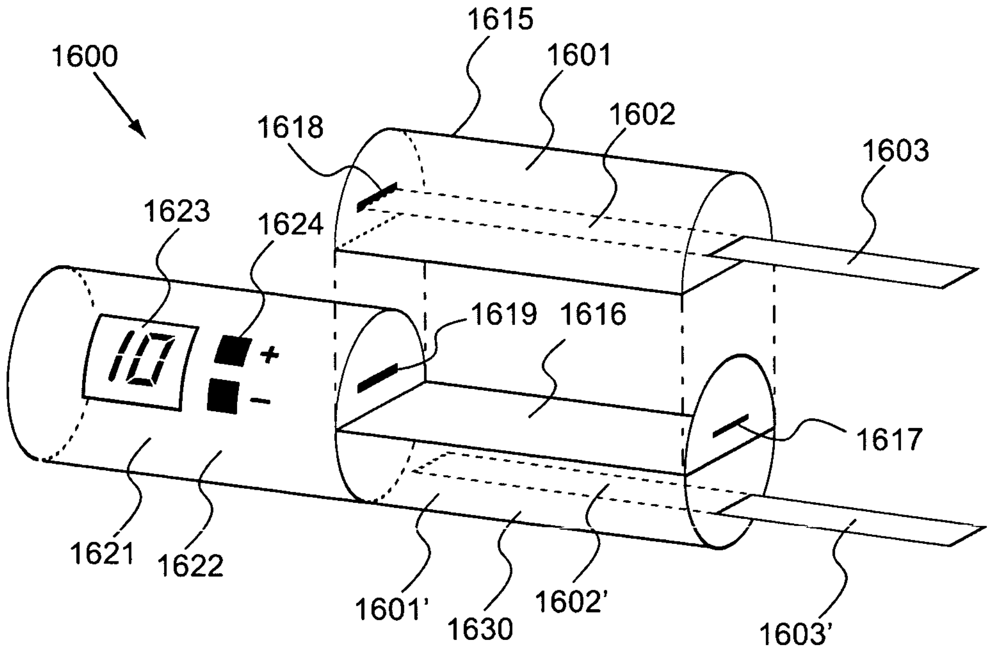
FIG. 16 is a schematic perspective view of an ion delivery device having an exchangeable cartridge.

FIG. 16 illustrates one embodiment of a device 1600 which comprises a cartridge 1615, a main body 1621, and a counter electrode 1630.

The cartridge 1615 and the counter electrode 1630 may comprise, respectively, an electrolyte 1601, 1601', an electrode 1602, 1602' and an ion conductor 1603, 1603'.

The main body 1621 may be permanently attached to the counter electrode 1630.

The main body 1621 may comprise a power source 1622 and a control unit. The control unit may comprise a user interface, which may comprise one or more input and/or output devices, which may be optical, mechanical, audible and/or tactile.

The interface may, according to one embodiment, be a display 1623 and control means 1624. The control means 1624 may include buttons, a lever or a revolving device. The display 1623 may be arranged to display the voltage applied, or e.g. the amount of ions delivered.

The power source may be a battery, which may be integrated, removable or externally connectable to the control electronics. The integrated battery may be rechargeable. The power source may also be an external power source, such as electricity from a wall socket, to which the device 1600 may be connected by a wire.

The main body may further comprise a receptacle 1616 for receiving the cartridge 1615. The receptacle 1616 may be formed as a cradle for receiving the cartridge 1615. The receptacle may comprise an electrical connector 1619 for connecting the electronic control to the cartridge. The cartridge may comprise a corresponding electrical connector 1618 for engagement with the electrical connector 1619.

The receptacle 1616 may further comprise an opening 1617 at one end of the cradle for inserting the ion conductor 1603 of the cartridge.

The device 1600 may be used as an electronically controlled pipette, or a "smart pipette". The cartridge may then be filled or pre-filled, with an electrolyte containing ions to be delivered into a test tube, a flask, a cell culture plate, an organ etc. The cartridge may be placed in the receptacle.

The second portion 1630 may act as a counter electrode. By controlling the voltage applied, and hence the potential difference over the devices the delivery of ions from the cartridge electrolyte 1601 to the outside of the encapsulation or target region, i.e. for instance the liquid in the flask, or the cells on the cell culture plate. The ion conductor 1603' of the second portion must also be in ionic contact with the target region. Hence by adjusting/controlling the voltage the delivery of ions may be specifically controlled. The cartridge ion conductor 1603 may hence be a dispensing ion conductor.

The ion conductor 1603 may, according to one alternative be an integrated part of the receptacle/control electronics. The cartridge 1615 may hence only comprise the electrode and the electrolyte and the ion conductor may be connected to the cartridge by e.g. punching into it.

Other configurations and uses of the "smart pipette" may also be conceivable by a person skilled in the art.

The parts of the smart pipette may, according to one embodiment, be separate, i.e. the ion delivery portion may substantially be a device as shown in FIG. 1*a*. The counter electrode portion may be another FIG. 1*a* device or simply a wire. The control electronics may be e.g. a laboratory power supply device or similar, with which it is possible to adjust/control the voltage applied to the delivery portion and counter electrode portion.

FIGS. 17*a*-17*d* illustrates different control schemes for the different connections of control units to the ion delivery and/or extraction device.

A control unit may be a device capable of controlling the voltage applied to the device(s). The control unit may comprise a power source for the operation of the device(s). The control unit may also be separated from the power source, for instance the power source may be integrated with the device and the control system may be placed at a distance from the device. An external electronic system may be a laboratory power supply, controlled by a personal computer.

Figure 17A:
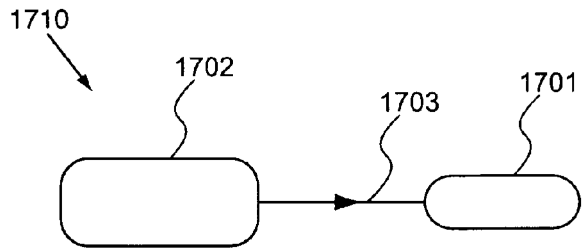
FIGS. 17*a*-17*e* are schematic block diagrams of different ion delivery device systems.
Figure 17B:
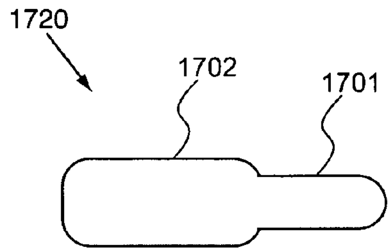

FIGS. 17*a* and 17*b* illustrates a system where the control unit 1702 is integrated with the ion delivery and/or extraction device 1701. By "integrated" is meant that the control unit 1702 may be arranged in the direct vicinity of the device (FIG. 17*b*) or placed at a short distance of a few centimeters away from the device (FIG. 17*a*). The connection between the device and the control unit in FIG. 17*a* may be a wire 1703, or multiple wires. The connection may also be wireless.

Figure 17C:
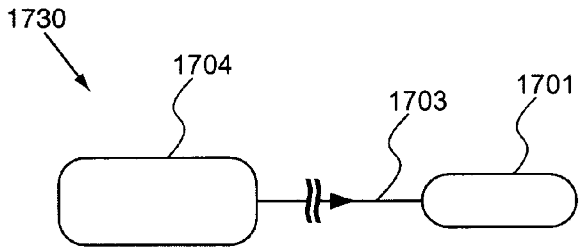

FIG. 17*c* illustrate that the control device 1704 may be placed at large distance from the device 1701. The device and control device may be connected by a wire 1703, or wires or be wireless.

Figure 17D:
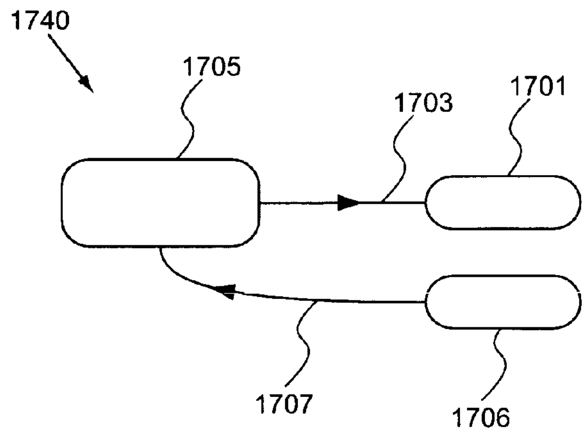

FIG. 17*d* illustrates that a sensor device 1706 may be connected to a control unit 1705. The control unit 1705 may, in turn, also be connected to an ion receiving and/or extraction device 1701. The sensor may be connected to the control device by a cable 1707. The device 1701 may be connected to the control device by a cable 1703. The connection may also be wireless.

Figure 17E:
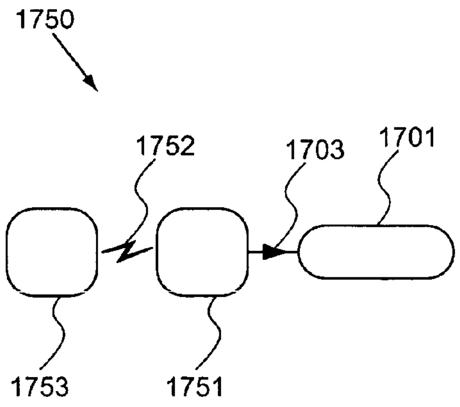

A first portion 1751 of a control device may, according to one embodiment, shown in FIG. 17*e*, be integrated with the device and a second portion 1753 may be separable from the first portion 1751. The connection 1752 between the first and second portions may be a cable or wireless.

Any number of devices 1701 may be connected to any number of control devices 1702, 1704, 1705.

Figure 18:
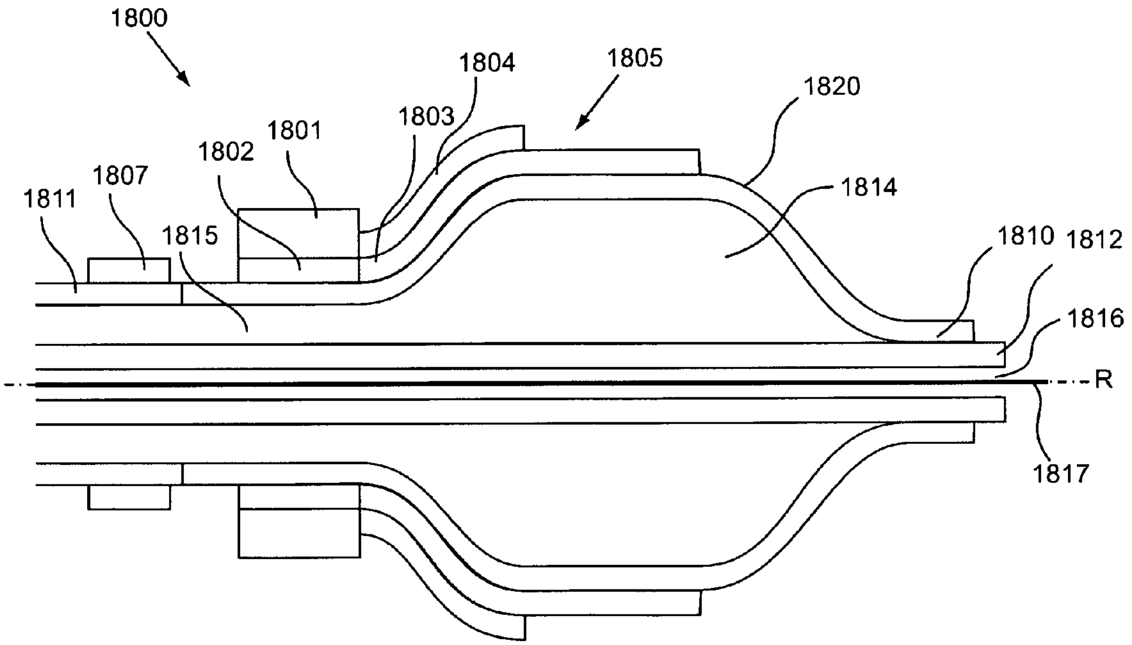
FIG. 18 is a schematic sectional view of a medical device provided with an ion delivery device.

FIG. 18 illustrates that an ion delivery and/or extraction device may be integrated with or attached to a medical device in order to improve/increase or alter the functionality of the medical device. The device may hence be shaped to fit with the medical device, cp. FIG. 1*a*.

The medical device may be a surgical tool, a catheter or catheter system as well as devices positioned by means of catheters, such as clamps, forceps, stents, clips, expandable tubes, constricting tubes etc.

The medical device in FIG. 18 may be a standard PTCA (percutaneous transluminal coronary angioplasty) balloon catheter 1800, having an ion delivery and/or extraction device attached to an outwardly facing portion 1820 of the balloon catheter body. The catheter may comprise a dilation balloon portion 1810, a proximal portion 1811 and a distal portion 1812. The catheter further comprises an inflation lumen 1814 and an inflation channel 1815. The catheter may be brought into the correct position, by pushing the catheter over the guide wire 1817 through guide wire lumen 1816.

An ion delivery and/or extraction device may be positioned onto the balloon inflation area to release ions into a target region 1805. The encapsulated electrolyte 1801, comprising the source electrode 1802 may be arranged at the proximal portion 1811 of the dilation balloon shaft 1810. The ion conductor 1803 may be arranged such that it substantially follows the expansion of the balloon portion. The ion conductor 1803 may be provided with an ionic insulation 1804. The ionic insulation may be arranged to partially cover the ion conductor. A counter electrode 1807 may be arranged anywhere in the proximity of the target region 1805. The counter electrode may be arranged on the catheter or be arranged separately.

The electric control of the device may be achieved by the same means as described above.

Figure 19A:
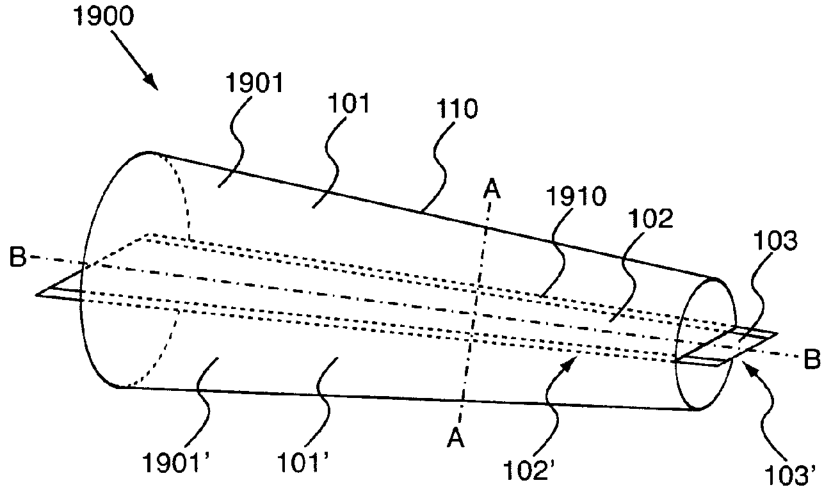
FIG. 19*a* is a schematic perspective view of a multiple electrode tubular ion delivery device.
Figure 19B:
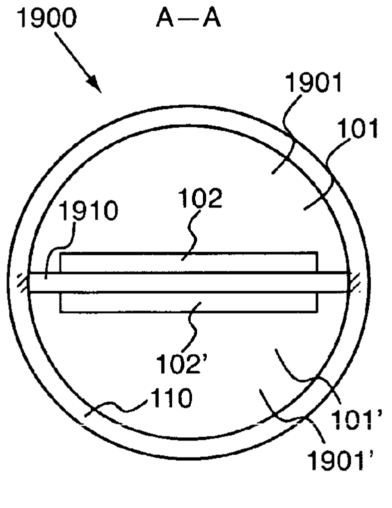
FIG. 19*b* is a cross-section along the line A-A of FIG. 19*a*.
Figure 19C:
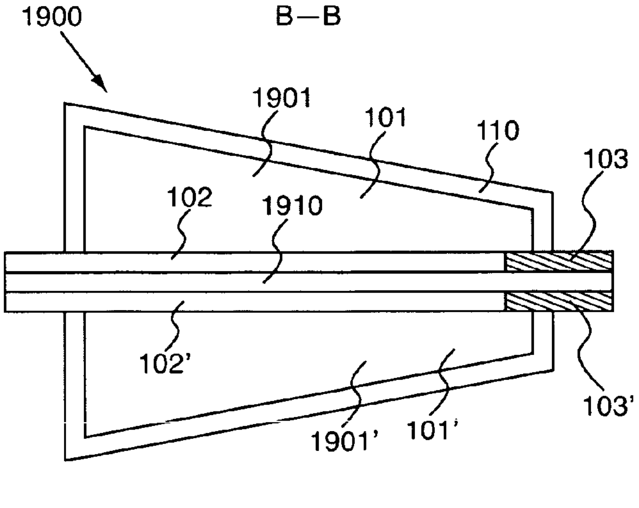
FIG. 19*c* is a cross-section along the line B-B of FIG. 19*a*.

FIG. 19*a* illustrates an alternative embodiment of the multi-chamber device. FIG. 19*b* is a cross-section along the line A-A and FIG. 19*c* is a cross-section along the line B-B.

The device 1900 may, according to this embodiment, comprise a first 1901 and a second 1901' chamber arranged adjacent to each other.

The chambers may be divided by an inner wall 1910. The inner wall 1910 may be both ionically and electrically insulating. The inner wall 1910 may further be impermeable, i.e. does not allow for any physical transport of molecules from one electrolyte to the other.

The inner wall 1910 may be of the same material as the encapsulation 110 or a different material.

The first chamber 1901 may comprise a first electrolyte 101, a first electrode 102 and a first ion conductor 103 arranged to deliver and/or extract ions to/from a target region (not shown) outside the encapsulation 110. The second chamber 1901' may comprise a second electrolyte 101', which may be the same as, or different from, the first electrolyte, a second electrode 102' and a second ion conductor 103' arranged to deliver and/or extract ions from a target region 104 outside the encapsulation 110.

The encapsulation 110 may be formed by an electronically and ionically insulating material, which essentially completely encapsulates the electrolyte. The body of the encapsulation 110 may be formed as a truncated cylinder.

The first 102 and second 102' electrode may protrude from one face of the device 1900. The protrusion of the electrodes 102 and 102' allows for electronic connection to the device. The first 103 and the second 103' ion conductor may protrude from one face from the device 1900.

According to this alternative embodiment, the ion pump may be operated by applying a voltage between the source electrode 102 and the counter electrode 102'.

The device may be manufacturing by printing the electrodes 102 and 102' on each side of a substrate. The encapsulation 110 may then be injection-moulded around the electrodes 102, 102", the substrate may hence become the inner wall 1910. The electrolyte 101, 101' may then be filled through openings at the end of the encapsulation 110 where the electrodes protrude. After filling, the encapsulation may be melted together around the electrodes in order to encapsulate the electrolytes.

EXAMPLES OF APPLICATIONS

In the below a number of applications will be described, without being bound by theory. The exemplified applications should in no way be regarded as limiting the scope of the invention or the possible application areas.

Example 1

Neuro-Applications

The drug-delivery device may be designed to be used as a drug-delivery device capable of pin-point delivery of ions, neurotransmitters and drugs to specific areas in the brain or in the peripheral nervous system. Due to the potency of most drugs and neurotransmitters aimed for use in neuro-applications it is a huge benefit with local delivery achieved by the drug-delivery electrode. The drug-delivery electrode uses electronically controlled release of specific molecules rather than electro-impulses of existing electrophysiological probes used today.

Regulation of Hearing Capacity

An ion pump implant, based on the inventive device is expected to be able to locally deliver neurotransmitters like glutamate, acetylcholine, gamma-amino-butyric-acid (GABA) and aspartate as well as other pharmaceutical drugs into the perilymphatic system within the cochlea. This novel method of electronically induced molecular signaling aims to regulate activity of the hearing nerve, directly or indirectly to improve hearing or lower hearing sensitivity as well as stimulate regeneration of neurons after damage.

Example 2

CNS-Disorders

Epilepsy

An in vivo implant, based on the drug-delivery electrode is expected to be able to locally deliver inhibitory neurotransmitters like GABA or other antepileptic drugs to reduce or abolish epileptic seizures. Side effects of antiepileptic medication are a common problem and usually the physician needs to determine medical compliance by titration of the dose. Using the drug-delivery electrode, a higher level of control of dose is achieved, thus limiting possible side effects.

Parkinsons

In Parkinsons disease dopaminergic neurons have lost the ability to secrete dopamine leading to inhibition of signaling relays to the motor cortex and consequently to hypokinesia and tremor. Administred L-dopa is the most commonly used treatment to Parkinsons disease, where L-dopa is converted to dopamine in dopaminergic neurons. A serious drawback of orally administered L-dopa is that it is also converted to dopamine in peripheral tissue leading to adverse side-effects like hypotension, arrhythmia, nausea and hair loss.

An in vivo implant, based on the drug-delivery electrode is expected to be able to locally deliver drugs including dopamine with electronic control to the CNS to prevent the origination of unwanted side-effects common to orally or systemically administered drugs.

Alzheimers Disease

Reduced bio-synthesis of neurotransmitter acetylcholine has been associated with Alzheimers disease. An in vivo implant, based on the drug-delivery electrode is expected to be able to locally deliver acethylcholine to the CNS to reduce symptoms of disease.

Myasthenia Gravis

Myasthenia gravis is an autoimmune disorder where the immune system inappropriately produces antibodies towards the acethylcholine receptor at the post-synaptic neuromuscular junction and thus inhibits proper action of the neurotransmitter acethylcholine. An in vivo implant, based on the drug-delivery electrode is expected to be able to locally deliver acethylcholine to increase signal transmission to the muscle fiber.

Example 3

Muscle and Muscle Tonus Applications

Loss of control over muscle contraction is a huge medical problem. This is both for skeletal muscle that is voluntarily controlled or smooth muscle that is involuntarily controlled. The loss of control can be manifested as involuntary contractions or loss of muscle tonus. The device described herein may be applied as a stimuli device where electronic release of neurotransmitters can increase control and promote re-sensitization of muscles in the body where control as been lost due to medical problems.

Faciali Paresis

Facial paresis, or partial paralysis of the face is a condition that can arise after surgery, tumors, damage to the face or infections. It can also be idiopathic. Faciali paresis can be permanent but often disappears after 2-3 month or longer. The device described herein may be applied as a stimuli device where electronic release of neurotransmitters can increase control of the facial musculature and promote re-sensitization of the facial nerves.

Stroke

Stroke patients often experience loss of muscular control after a seizure. This can problem can arise in both voluntarily and involuntarily controlled muscles. One example is difficulties in initiate swallow movement. By using the device described herein, neurotransmitters like acetylcholine may be released in vivo, to promote increased control over muscles and re-sensitization of nerves.

Sphincter Muscles

Sphincter muscles are defined as any of the ring-like muscles surrounding and able to contract or close a bodily passage or opening. The ion pump implant may be used as an in vivo delivery electrode to deliver neurotransmitters like acetylcholine to achieve control and restore the function of the sphincters.

Urinary Tract

The internal and the external urethral sphincters serve the function of controlling the flow and dispersion of urine from the body. The internal is involuntarily controlled while the external is voluntarily controlled. Loss of muscle control or tonus of these sphincters is a problem associated with many pathological conditions of the urinary tract and leads to urine leakage. Loss of tonus of these sphincters can occur after surgery and it also occurs with age. By using the device described herein, neurotransmitters like acetylcholine can be released in vivo to promote increased control and re-sensitization to these sphincter muscles.

Anal and Rectal Sphincters

The internal and the external anal sphincters serve the function of expelling feces from the body. The internal is involuntarily controlled while the external is voluntarily controlled. Reduced control of these sphincters can be due to many disorders but also due to surgery and child-birth. Dysfunction of the anal sphincters is very inhibiting for patients. By using the device described herein, neurotransmitters like acetylcholine can be released in vivo to promote increased control and re-sensitization to these sphincter muscles.

Esophageal Sphincters

The upper esophageal sphincter is composed largely of a muscle that is closely associated with the larynx. When relaxed, as it is during swallowing, this muscle pulls the larynx forward and aids in routing food into the esophagus instead of the larynx. The lower esophageal sphincter is the muscle that surrounds the esophagus just as it enters the stomach. These sphincters close rapidly to prevent swallowed food or drink from leaking out of the stomach back into the esophagus or into the mouth. Achalasia is a disorder where the smooth muscle layer of the esophagus has impaired peristalsis (muscular ability to move food down the esophagus), and the lower esophageal sphincter fails to relax properly in response to swallowing. Loss of control of these sphincters can also lead to stomach acid reflux. By using the device described herein, neurotransmitters like acetylcholine can be released in vivo to promote increased control and re-sensitization to these sphincter muscles.

Pyloric Sphincter

The pyloric sphincter lets food to pass to the small intestine (duodenum) after digestion in the stomach. Dysfunction of the pyloric sphincter leads to duodenal reflux and stomach efflux, where stomach acid escapes to the intestine and bile salts and digested food can reflux to the stomach. By using the device described herein, neurotransmitters like acetylcholine can be released in vivo to promote increased control over the pyloric sphincter.

Example 4

Cardiac Applications

The heart is composed of cardiac muscle, an involuntary muscle tissue which is found only within this organ. The contractions of the heart are controlled by chemical impulses, which fire at a rate which controls the beat of the heart. Pacemaker cells, situated at pacemaker nodes create rhythmical impulses, thus directly control the heart rate. The sinoatrial node (SA node) is the primary pacemaker node. Conditions can arise where the heart can not maintain a steady heart rate and needs induction of impulses at the pacemaker nodes to beat. By using the drug-delivery electrode neurotransmitters can be injected to stimulate the pacemaker cells and facilitate control over contractions and heart rate. Norepinephrine can be used to increase heart rate, while acetylcholine decreases heart rate. The ionic homeostasis in the pacemaker cells is very important for their function. The the device described herein can be used to control the ion homeostasis by direct transport and release, thus further increases the therapeutical capabilities of the device.

The invention claimed is:

1. A device for electrically controlled transport of ions, comprising:

an enclosure having at least one channel therein for holding electrolyte;

an electrode arranged for contact with electrolyte in the channel;

an ion conductor comprising an ion conducting and electronically non-conductive material, arranged to contact the electrolyte in the channel, and protruding from within the enclosure to an exterior ion delivery portion, wherein the electrode comprises a conducting polymer, and the ion conductor material comprises a body of corresponding polymer that has been oxidized to render it electronically non-conductive.

2. A device as claimed in claim 1, further comprising a control unit arranged to control the transport of ions in the ion conductor, wherein the control unit is configured to be integrated with or connectable to the ion delivery and extraction device.

3. The device as claimed in claim 2, further comprising a sensor in communication with the control unit and arranged to provide feedback on at least one parameter to the control unit.

4. The device as claimed in claim 1, wherein the device is configured to be implanted into a body.

5. The device as claimed in claim 1, wherein the device is configured to be temporarily inserted into a body or brought into contact with the body.

6. A method of treating and preventing a disease or disorder in an animal by controlling the release of an active agent, the method comprising:

providing a device as claimed in claim 1, configured and dimensioned to be used within a body of an animal;

bringing the device into contact with the body of the animal; and applying a control signal to the device, thereby causing the active agent to be released from said ion conductor to the body of the animal.

7. The method as claimed in claim 6, further comprising using a sensor to directly or indirectly detect a physiological parameter, the release of the active agent or a biological response to the release, and adjusting the release of the active agent at least partially based on a signal from the sensor.

8. The method as claimed in claim 7, wherein the active agent comprises any one of acetylcholine, aspartate, dopamine, norepinephrine, serotonin, histamine, epinephrine, ATP, GTP, gamma-aminobuturic acid, glutamate, aspartate, glycine, tryptophan, adenine, guanine, cytosine, thymine, adenosine or combinations thereof.

* * * * *